United States Patent
Nitzan et al.

(10) Patent No.: US 12,005,214 B2
(45) Date of Patent: Jun. 11, 2024

(54) DEVICE AND METHOD FOR REGULATING PRESSURE IN A HEART CHAMBER

(71) Applicant: V-Wave Ltd., Caesarea (IL)

(72) Inventors: Yaacov Nitzan, Hertzelia (IL); Boaz Harari, Tel-Aviv (IL); Ascher Shmulewitz, Tel-Aviv (IL); Tovy Sivan, Kfar-Saba (IL)

(73) Assignee: V-Wave Ltd., Caesarea (IL)

( * ) Notice: Subject to any disclaimer, the term of this patent is extended or adjusted under 35 U.S.C. 154(b) by 627 days.

(21) Appl. No.: 16/866,377

(22) Filed: May 4, 2020

(65) Prior Publication Data

US 2020/0261705 A1   Aug. 20, 2020

Related U.S. Application Data

(60) Continuation of application No. 15/650,783, filed on Jul. 14, 2017, now Pat. No. 10,639,459, which is a division of application No. 14/227,982, filed on Mar. 27, 2014, now Pat. No. 9,707,382, which is a continuation of application No. 13/108,880, filed on May 16, 2011, now Pat. No. 8,696,611, which is a
(Continued)

(51) Int. Cl.
*A61M 27/00* (2006.01)
*A61F 2/24* (2006.01)

(52) U.S. Cl.
CPC ......... *A61M 27/002* (2013.01); *A61F 2/2412* (2013.01); *A61F 2/2418* (2013.01); *A61M 27/006* (2013.01); *A61F 2002/249* (2013.01); *A61F 2220/0058* (2013.01); *A61F 2220/0066* (2013.01); *A61F 2230/0013* (2013.01); *A61F 2230/0078* (2013.01)

(58) Field of Classification Search
CPC .................. A61F 2/2412; A61F 2/2418; A61F 2002/249; A61F 2230/0013; A61F 2230/0078; A61M 27/002
See application file for complete search history.

(56) References Cited

U.S. PATENT DOCUMENTS

| | | |
|---|---|---|
| 3,852,334 A | 12/1974 | Dusza et al. |
| 3,874,388 A | 4/1975 | King et al. |
| 3,952,334 A | 4/1976 | Bokros et al. |

(Continued)

FOREIGN PATENT DOCUMENTS

| | | |
|---|---|---|
| AU | 2003291117 B2 | 4/2009 |
| CA | 2378920 A1 | 2/2001 |

(Continued)

OTHER PUBLICATIONS

U.S. Appl. No. 09/839,643 / U.S. Pat. No. 8,091,556, filed Apr. 20, 2001 / Jan. 10, 2012.

(Continued)

*Primary Examiner* — Ariana Zimbouski
(74) *Attorney, Agent, or Firm* — Eversheds Sutherland (US) LLP; Christopher C. Bolten; Albert K. Heng

(57) ABSTRACT

A device for regulating blood pressure in a heart chamber is provided. The device includes a shunt positionable within a septum of the heart. The shunt is designed for enabling blood flow between a loft heart chamber and a right heart chamber, wherein the flow rate capacity of the device is mostly a function of pressure in the left heart chamber.

24 Claims, 9 Drawing Sheets

Related U.S. Application Data continuation of application No. PCT/IL2010/000354, filed on May 4, 2010.

(60) Provisional application No. 61/240,667, filed on Sep. 9, 2009, provisional application No. 61/175,073, filed on May 4, 2009.

(56) References Cited

U.S. PATENT DOCUMENTS

| | | | |
|---|---|---|---|
| 4,364,395 A | 12/1982 | Redmond et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,702 A | 7/1991 | Taheri |
| 5,035,706 A | 7/1991 | Giantureo et al. |
| 5,037,427 A | 8/1991 | Harada et al. |
| 5,089,005 A | 2/1992 | Harada |
| 5,186,431 A | 2/1993 | Tamari |
| 5,197,978 A | 3/1993 | Hess |
| 5,234,447 A | 8/1993 | Kaster et al. |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,957,949 A | 9/1999 | Leonhardt et al. |
| 5,990,379 A | 11/1999 | Gregory |
| 6,007,544 A | 12/1999 | Kim |
| 6,027,518 A | 2/2000 | Gaber |
| 6,039,755 A | 3/2000 | Edwin et al. |
| 6,039,759 A | 3/2000 | Carpentier et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,029 B1 | 4/2001 | Thill et al. |
| 6,214,039 B1 | 4/2001 | Banas et al. |
| 6,217,541 B1 | 4/2001 | Yu |
| 6,221,096 B1 | 4/2001 | Aiba et al. |
| 6,231,587 B1 | 5/2001 | Makower |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,290,728 B1 | 9/2001 | Phelps et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford, III et al. |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 | 5/2003 | Martin |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,616,675 B1 | 9/2003 | Evard et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,645,220 B1 | 11/2003 | Huter et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak |
| 6,923,829 B2 | 8/2005 | Boyle et al. |
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |
| 7,306,756 B2 | 12/2007 | Edwin et al. |
| 7,402,899 B1 | 7/2008 | Whiting et al. |
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |

(56) References Cited

U.S. PATENT DOCUMENTS

| | | |
|---|---|---|
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,216,398 B2 | 7/2012 | Bledsoe et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,207,087 B2 | 2/2019 | Keren et al. |
| 10,207,807 B2 | 2/2019 | Moran et al. |
| 10,251,740 B2 | 4/2019 | Eigler et al. |
| 10,251,750 B2 | 4/2019 | Alexander et al. |
| 10,265,169 B2 | 4/2019 | Desrosiers et al. |
| 10,299,687 B2 | 5/2019 | Nabutovsky et al. |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,583,002 B2 | 3/2020 | Lane et al. |
| 10,639,459 B2 | 5/2020 | Nitzan et al. |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,940,296 B2 | 3/2021 | Keren |
| 11,109,988 B2 | 9/2021 | Rosen et al. |
| 11,135,054 B2 | 10/2021 | Nitzan et al. |
| 11,234,702 B1 | 2/2022 | Eigler et al. |
| 11,253,353 B2 | 2/2022 | Levi et al. |
| 11,255,379 B2 | 2/2022 | Baskin et al. |
| 11,291,807 B2 | 4/2022 | Eigler et al. |
| 11,304,831 B2 | 4/2022 | Nae et al. |
| 11,382,747 B2 | 7/2022 | Rottenberg et al. |
| 11,458,287 B2 | 10/2022 | Eigler et al. |
| 11,497,631 B2 | 11/2022 | Rosen et al. |
| 11,607,327 B2 | 3/2023 | Nae et al. |
| 11,612,385 B2 | 3/2023 | Nae et al. |
| 11,690,976 B2 | 7/2023 | Yacoby et al. |
| 11,813,386 B2 | 11/2023 | Nae et al. |
| 2001/0007956 A1 | 7/2001 | Letac et al. |
| 2001/0021872 A1 | 9/2001 | Bailey et al. |
| 2002/0051730 A1 | 5/2002 | Bodnar et al. |
| 2002/0099431 A1 | 7/2002 | Armstrong et al. |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2002/0183628 A1 | 12/2002 | Reich et al. |
| 2003/0028213 A1 | 2/2003 | Thill et al. |
| 2003/0045902 A1 | 3/2003 | Weadock |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0139819 A1 | 7/2003 | Beer et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0073242 A1 | 4/2004 | Chanduszko |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |

(56) References Cited

U.S. PATENT DOCUMENTS

| | | |
|---|---|---|
| 2004/0147886 A1 | 7/2004 | Bonni |
| 2004/0147969 A1 | 7/2004 | Mann et al. |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0125032 A1 | 6/2005 | Whisenant et al. |
| 2005/0137682 A1 | 6/2005 | Justino |
| 2005/0148925 A1* | 7/2005 | Rottenberg ........... A61F 2/2442 604/9 |
| 2005/0165344 A1 | 7/2005 | Dobak, III |
| 2005/0182486 A1 | 8/2005 | Gabbay |
| 2005/0267524 A1 | 12/2005 | Chanduszko |
| 2005/0283231 A1 | 12/2005 | Haug et al. |
| 2005/0288596 A1 | 12/2005 | Eigler et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0025857 A1 | 2/2006 | Bergheim et al. |
| 2006/0052821 A1 | 3/2006 | Abbott et al. |
| 2006/0111660 A1 | 5/2006 | Wolf et al. |
| 2006/0111704 A1 | 5/2006 | Brenneman et al. |
| 2006/0116710 A1 | 6/2006 | Corcoran et al. |
| 2006/0122522 A1 | 6/2006 | Chavan et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0073337 A1 | 3/2007 | Abbott et al. |
| 2007/0129756 A1 | 6/2007 | Abbott et al. |
| 2007/0191863 A1* | 8/2007 | De Juan, Jr. ......... A61F 9/0008 606/108 |
| 2007/0213813 A1 | 9/2007 | Von Segesser et al. |
| 2007/0249985 A1 | 10/2007 | Brenneman et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0171944 A1 | 7/2008 | Brenneman et al. |
| 2008/0177300 A1 | 7/2008 | Mas et al. |
| 2008/0243081 A1 | 10/2008 | Nance et al. |
| 2008/0262602 A1 | 10/2008 | Wilk et al. |
| 2008/0264102 A1 | 10/2008 | Berra |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1* | 8/2009 | Boudjemline ........... D04C 3/48 623/1.2 |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1* | 3/2010 | Celermajer ......... A61M 27/002 623/1.26 |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson et al. |
| 2010/0191326 A1 | 7/2010 | Alkhatib |
| 2010/0249491 A1 | 9/2010 | Farnan et al. |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324652 A1 | 12/2010 | Aurilia et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1* | 4/2011 | Fischell ............... A61F 2/91 623/1.15 |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0251675 A1 | 10/2011 | Dwork |
| 2011/0257723 A1 | 10/2011 | McNamara |
| 2011/0264191 A1 | 10/2011 | Rothstein |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022507 A1 | 1/2012 | Najafi et al. |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | Von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1 | 6/2012 | Nitzan et al. |
| 2012/0179172 A1 | 7/2012 | Paul, Jr. et al. |
| 2012/0190991 A1 | 7/2012 | Bornzin et al. |
| 2012/0265296 A1 | 10/2012 | McNamara et al. |
| 2012/0271277 A1 | 10/2012 | Fischell et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0096965 A1 | 4/2013 | Pappas et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2013/0331864 A1 | 12/2013 | Jelich et al. |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry, III et al. |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |

(56) References Cited

U.S. PATENT DOCUMENTS

| | | |
|---|---|---|
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2014/0364941 A1 | 12/2014 | Edmiston et al. |
| 2015/0005810 A1 | 1/2015 | Center et al. |
| 2015/0034217 A1 | 2/2015 | Vad |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0112383 A1 | 4/2015 | Sherman et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0313599 A1 | 11/2015 | Johnson et al. |
| 2015/0335801 A1 | 11/2015 | Farnan et al. |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forcucci et al. |
| 2016/0045311 A1 | 2/2016 | McCann et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0056171 A1 | 3/2017 | Cooper et al. |
| 2017/0112624 A1 | 4/2017 | Patel |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165062 A1 | 6/2017 | Rothstein |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0340460 A1 | 11/2017 | Rosen et al. |
| 2017/0348100 A1 | 12/2017 | Lane et al. |
| 2018/0028314 A1 | 2/2018 | Ekvall et al. |
| 2018/0099128 A9 | 4/2018 | McNamara et al. |
| 2018/0104053 A1 | 4/2018 | Alkhatib et al. |
| 2018/0110609 A1 | 4/2018 | Ehnes et al. |
| 2018/0125630 A1 | 5/2018 | Hynes et al. |
| 2018/0130988 A1 | 5/2018 | Nishikawa et al. |
| 2018/0243071 A1 | 8/2018 | Eigler et al. |
| 2018/0256865 A1 | 9/2018 | Finch et al. |
| 2018/0263766 A1 | 9/2018 | Nitzan et al. |
| 2018/0280667 A1 | 10/2018 | Keren |
| 2018/0280668 A1 | 10/2018 | Alaswad |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015103 A1 | 1/2019 | Sharma |
| 2019/0015188 A1 | 1/2019 | Eigler et al. |
| 2019/0021861 A1 | 1/2019 | Finch |
| 2019/0083076 A1 | 3/2019 | Alanbaei |
| 2019/0110911 A1 | 4/2019 | Nae et al. |
| 2019/0239754 A1 | 8/2019 | Nabutovsky et al. |
| 2019/0254814 A1 | 8/2019 | Nitzan et al. |
| 2019/0262118 A1 | 8/2019 | Eigler et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0197178 A1 | 6/2020 | Vecchio |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2021/0022507 A1 | 1/2021 | Williams |
| 2021/0052378 A1 | 2/2021 | Nitzan et al. |
| 2021/0100665 A1 | 4/2021 | Nae et al. |
| 2021/0121179 A1 | 4/2021 | Ben-David et al. |
| 2022/0008014 A1 | 1/2022 | Rowe et al. |
| 2022/0211361 A1 | 7/2022 | Rolando et al. |
| 2022/0304803 A1 | 9/2022 | Guyenot et al. |

FOREIGN PATENT DOCUMENTS

| | | |
|---|---|---|
| CN | 101505680 A | 8/2009 |
| CN | 105555204 A | 5/2016 |
| CN | 108451569 A | 8/2018 |
| EP | 1987777 A2 | 11/2008 |
| EP | 2238933 A1 | 10/2010 |
| EP | 2305321 A1 | 4/2011 |
| EP | 1965842 B1 | 11/2011 |
| EP | 3400907 A1 | 11/2018 |
| FR | 2827153 A1 | 1/2003 |
| WO | WO-9531945 A1 | 11/1995 |
| WO | WO-9702850 A1 | 1/1997 |
| WO | WO-9727898 A1 | 8/1997 |
| WO | WO-9960941 A1 | 12/1999 |
| WO | WO-0044311 A2 | 8/2000 |
| WO | WO-0050100 A1 | 8/2000 |
| WO | WO-0110314 A2 | 2/2001 |
| WO | WO-0126585 A1 | 4/2001 |
| WO | WO-0191828 A2 | 12/2001 |
| WO | WO-0226281 A1 | 4/2002 |
| WO | WO-02071974 A2 | 9/2002 |
| WO | WO-02087473 A1 | 11/2002 |
| WO | WO-03053495 A2 | 7/2003 |
| WO | WO-2005027752 A1 | 3/2005 |
| WO | WO-2005074367 A2 | 8/2005 |
| WO | WO-2006127765 A1 | 11/2006 |
| WO | WO-2007083288 A2 | 7/2007 |
| WO | WO-2008055301 A1 | 5/2008 |
| WO | WO-2008070797 A2 | 6/2008 |
| WO | WO-2009029261 A1 | 3/2009 |
| WO | WO-2010128501 A1 | 11/2010 |
| WO | WO-2010129089 A2 | 11/2010 |
| WO | WO-2010139771 A2 | 12/2010 |
| WO | WO-2010139771 A3 | 1/2011 |
| WO | WO-2011062858 A1 | 5/2011 |

(56) References Cited

FOREIGN PATENT DOCUMENTS

| WO | WO-2013096965 A1 | 6/2013 |
|---|---|---|
| WO | WO-2013172474 A1 | 11/2013 |
| WO | WO-2016178171 A1 | 11/2016 |
| WO | WO-2017118920 A1 | 7/2017 |
| WO | WO-2018158747 A1 | 9/2018 |
| WO | WO-2019015617 A1 | 1/2019 |
| WO | WO-2019085841 A1 | 5/2019 |
| WO | WO-2019109013 A1 | 6/2019 |
| WO | WO-2019142152 A1 | 7/2019 |
| WO | WO-2019179447 A1 | 9/2019 |
| WO | WO-2019218072 A1 | 11/2019 |
| WO | WO-2020206062 A1 | 10/2020 |
| WO | WO-2020257530 A1 | 12/2020 |
| WO | WO-2021050589 A1 | 3/2021 |
| WO | WO-2021113670 A1 | 6/2021 |
| WO | WO-2021212011 A2 | 10/2021 |
| WO | WO-2021224736 A1 | 11/2021 |
| WO | WO-2022046921 A1 | 3/2022 |
| WO | WO-2022076601 A1 | 4/2022 |
| WO | WO-2022091018 A1 | 5/2022 |
| WO | WO-2022091019 A1 | 5/2022 |
| WO | WO-2022103973 A1 | 5/2022 |

OTHER PUBLICATIONS

U.S. Appl. No. 10/597,666 / U.S. Pat. No. 8,070,708, filed Jun. 20, 2007 / Dec. 6, 2011.
U.S. Appl. No. 12/223,080 / U.S. Pat. No. 9,681,948, filed Jul. 16, 2014 / Jun. 20, 2017.
U.S. Appl. No. 13/107,832 / U.S. Pat. No. 8,235,933, filed May 13, 2011 / Aug. 7, 2012.
U.S. Appl. No. 13/107,843 / U.S. Pat. No. 8,328,751, filed May 13, 2011 / Dec. 11, 2012.
U.S. Appl. No. 13/108,672 / U.S. Pat. No. 9,724,499, filed May 16, 2011 / Aug. 8, 2017.
U.S. Appl. No. 13/108,698, filed Jun. 16, 2011.
U.S. Appl. No. 13/108,850, filed May 16, 2011.
U.S. Appl. No. 13/108,880 / U.S. Pat. No. 8,696,611, filed May 16, 2011 / Apr. 15, 2014.
U.S. Appl. No. 13/193,309 / U.S. Pat. No. 9,629,715, filed Jul. 28, 2011 / Apr. 25, 2017.
U.S. Appl. No. 13/193,335 / U.S. Pat. No. 9,034,034, filed Jul. 28, 2011 / May 19, 2015.
U.S. Appl. No. 13/708,794 / U.S. Pat. No. 9,943,670, filed Dec. 7, 2012 / Apr. 17, 2018.
U.S. Appl. No. 14/154,080 / U.S. Pat. No. 10,207,807, filed Jan. 13, 2014 / Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982 / U.S. Pat. No. 9,707,382, filed Mar. 27, 2014 / Jul. 18, 2017.
U.S. Appl. No. 14/282,615 / U.S. Pat. No. 9,713,696, filed May 20, 2014 / Jul. 25, 2017.
U.S. Appl. No. 14/712,801 / U.S. Pat. No. 9,980,815, filed May 14, 2015 / May 29, 2018.
U.S. Appl. No. 15/449,834 / U.S. Pat. No. 10,076,403, filed Mar. 3, 2017 / Sep. 18, 2018.
U.S. Appl. No. 15/492,852 / U.S. Pat. No. 10,368,981, filed Apr. 20, 2017 / Aug. 6, 2019.
U.S. Appl. No. 15/570,752, filed Oct. 31, 2017.
U.S. Appl. No. 15/608,948, filed May 30, 2017.
U.S. Appl. No. 15/624,314 / U.S. Pat. No. 10,357,357, filed Jun. 15, 2017 / Jul. 23, 2019.
U.S. Appl. No. 15/650,783 / U.S. Pat. No. 10,639,459, filed Jul. 14, 2017 / May 5, 2020.
U.S. Appl. No. 15/656,936 / U.S. Pat. No. 10,478,594, filed Jul. 21, 2017 / Nov. 19, 2019.
U.S. Appl. No. 15/668,622 / U.S. Pat. No. 10,463,490, filed Aug. 3, 2017 / Nov. 5, 2019.
U.S. Appl. No. 15/798,250, filed Oct. 30, 2017.
U.S. Appl. No. 16/130,978 / U.S. Pat. No. 10,251,740, filed Sep. 13, 2018 / Apr. 9, 2019.
U.S. Appl. No. 16/130,988, filed Sep. 13, 2018.
U.S. Appl. No. 16/205,213, filed Nov. 29, 2018.
U.S. Appl. No. 16/374,698, filed Apr. 3, 2019.
U.S. Appl. No. 16/395,209, filed Apr. 25, 2019.
U.S. Appl. No. 16/408,419, filed May 9, 2019.
U.S. Appl. No. 16/505,624, filed Jul. 8, 2019.
U.S. Appl. No. 16/686,013, filed Nov. 15, 2019.
U.S. Appl. No. 16/672,420, filed Nov. 1, 2019.
U.S. Appl. No. 16/866,377, filed May 4, 2020.
U.S. Appl. No. 16/875,652, filed May 15, 2020.
U.S. Appl. No. 16/876,640, filed May 18, 2020.
U.S. Appl. No. 16/878,228, filed May 19, 2020.
Ando, et al., Left ventricular decompression through a patent foramen ovale in a patient with hypertrophic cardiomyopathy: A case report, Cardiovascular Ultrasound, 2: 1-7 (2004).
Article 34 Amendments dated May 28, 2013 in related International PCT Patent Appl No. PCT/IB2012/001859.
Article 34 Amendments dated Nov. 27, 2012, as filed in related Int'l PCT Application No. PCT/IL2011/000958.
"Atrium Advanta V12, Balloon Expandable Covered Stent, Improving Patient Outcomes with An Endovascular Approach," Brochure, 8 pages, Getinge (2017).
Boehm, et al., Balloon Atrial Septostomy: History and Technique, Images Paeditr. Cardiol., 8(1):8-14(2006).
Braunwald, Heart Disease, Chapter 6, pp. 186.
Bridges, et al., The Society of Thoracic Surgeons Practice Guideline Series: Transmyocardial Laser Revascularization, Ann Thorac Surg., 77:1494-1502 (2004).
Bristow, et al., Improvement in cardiac myocite function by biological effects of medical therapy: a new concept in the treatment of heart failure, European Heart Journal 16 (Suppl.F): 20-31 (1995).
Case, et al., Relief of High Left-Atrial Pressure in Left-Ventricular Failure, Lancet, Oct. 17, 1964 (pp. 841-842).
Coats, et al., Controlled Trial of Physical Training in Chronic Heart Failure: Exercise Performance, Hemodynamics, Ventilation, and Autonomic Function, Circulation, 85: 2119-2131 (1992).
Davies, et al., Reduced Contraction and Altered Frequency Response of Isolated Ventricular Myocytes From Patients With Heart Failure, Circulation, 92: 2540-2549 (1995).
Del Trigo et al., Unidirectional Left-To-Right Interatrial Shunting for Treatment of Patients with Heart Failure with Reduced Ejection Fraction: a Safety and Proof-of-Principle Cohort Study, Lancet, 387:1290-1297 (Mar. 26, 2016).
Drexel, et al., The Effects of Cold Work and Heat Treatment on the Properties of Nitinol Wire, Proceedings of the International Conference on Shape Memory and Superelastic Technologies, May 7-11, 2006, Pacific Grove, California, USA (pp. 447-454).
Eigler, et al., Implantation and Recovery of Temporary Metallic Stents in Canine Coronary Arteries, JACC, 22(4):1207-1213 (1993).
Ennezat, et al., An unusual case of low-flow, low gradient severe aortic stenosis: Left-to-right shunt due to atrial septal defect, Cardiology, 113(2):146-148, (2009).
Ewert, et al., Acute Left Heart Failure After Interventional Occlusion of An Artial Septal Defect, Z Kardiol, 90(5): 362-366 (May 2001).
Ewert, et al., Masked Left Ventricular Restriction in Elderly Patients with Atrial Septal Defects: A Contraindication for Closure, Catherization and Cardiovascular Interventions, 52: 177-180 (2001).
Ewert, et al., Masked Left Ventricular Restriction in Elderly Patients With Atrial Septal Defects: A Contraindication for Closure?, Catheterization and Cardiovascular Intervention, 60: 1245-1249,(1995) Abstract.
Extended European Search Report dated Jan. 8, 2015 in EP Patent Appl No. 10772089.8. (0530).
Extended European Search Report dated Sep. 19, 2006 in EP Patent Appl No. 16170281.6 (0731).
Extended European Search Report dated Mar. 29, 2019 in EP Patent Appl. Serial No. EP16789391, 10 pages (1830).
Geiran, et al., Changes in cardiac dynamics by opening an interventricular shunt in dogs, J. Surg. Res. 48(1): 6-12 (1990).

(56) References Cited

OTHER PUBLICATIONS

Gelernter-Yaniv, et al., Transcatheter ClosureoOf Left-To-Right Interatrial Shunts to Resolve Hypoxemia, Congenit. Heart Dis. 31(1): 47-53 (Jan. 2008).
Gewillig, et al., Creation with a stent of an unrestrictive lasting atrial communication, Cardio. Young 12(4): 404-407 (2002).
Hasenfub, et al., A Transcatheter Intracardiac Shunt Device for Heart Failure with Preserved Ejection Fraction (Reduce LAP-HF): A Multicentre, Open-Label, Single-Arm, Phase 1 Trial, www.thelancet.com, 387:1298-1304 (2016).
International Search Report & Written Opinion dated Nov. 7, 2016 in Int'l PCT Patent Appl. Serial No. PCT/IB2016/052561 (1810).
International Search Report & Written Opinion dated May 29, 2018 in Int'l PCT Patent Appl. Serial No. PCT/IB2018/051385 (1310).
International Search Report & Written Opinion dated Feb. 6, 2013 in Int'l PCT Patent Appl No. PCT/IB2012/001859, 12 pages (0810).
International Search Report & Written Opinion dated May 13, 2019 in Int'l PCT Patent Appl No. PCT/IB2019/050452, 16 pages (1610).
International Search Report & Written Opinion dated Aug. 28, 2012 in Int'l PCT Patent Appl No. PCT/IL2011/000958, 16 pages (0710).
International Search Report & Written Opinion dated Mar. 19, 2015 in Int'l PCT Patent Appl Serial No. PCT/IB2014/002920 (0810).
International Search Report & Written Opinion dated May 29, 2018 in Int'l PCT Patent Appl. Serial No. PCTIB2018/051355 (1310).
International Search Report & Written Opinion dated Feb. 7, 2020 in Int'l PCT Patent Appl. Serial No. PCT/IB2019/060257 (1410).
International Search Report & Written Opinion dated Oct. 26, 2007 in International PCT Patent Application Serial No. PCT/IB07/50234 (0610).
International Search Report dated Apr. 7, 2008 received from the International Searching Authority of the Patent Cooperation Treaty Re.: PCT/IL05/00131 (0410).
International Search Report dated Aug. 25, 2010, in Intl PCT Patent Appl. No. PCT/IL2010/000354, (1 pg) (0510).
International search report dated Sep. 20, 2016 in Int'l PCT Patent Appl No. PCT/IB2016/052561 (1810).
ISR & Written Opinion dated Feb. 16, 2015 in Int'l PCT Patent Appl. Serial No. PCT/IB2014/001771 (0910).
Keren, et al. Methods and Apparatus for Reducing Localized Circulatory System Pressure,., Jan. 7, 2002 (pp. 16).
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer, et al., Controlled Trial of Captopril in Chronic Heart Failure: A Rest and Exercise Hemodynamic Study, Circulation, 67(4): 807-816, 1983.
Lai et al., Bidirectional Shunt Through a Residual Atrial Septal Defect After Percutaneous Transvenous Mitral Commissurotomy, Cadiology, 83(3): 205-207 (1993).
Lemmer, et al., Surgical Implications of Atrial Septal Defect Complicating Aortic Balloon Valvuloplasty, Ann. thorac. Surg, 48(2):295-297 (Aug. 1989).
Merck Index, 1759 and 3521 (11th ed. 1989).
Merriam-Webster OnLine Dictionary, Definition of "chamber", printed Dec. 20, 2004.
Park Blade Septostomy Catheter Instructions for Use, Cook Medical, 28 pages, Oct. 2015.
Park, et al., Blade Atrial Septostomy: Collaborative Study, Circulation, 66(2):258-266 (1982).
Partial International Search dated Aug. 17, 2017 in Int'l PCT Patent Appl. Serial No. PCT/IB2017/053188.
Partial Supplemental European Search Report dated Dec. 11, 2018 in EP Patent Appl. Serial No. 16789391.6 (1830).
Rosenquist et al., Atrial Septal Thickness and Area in Normal Heart Specimens and in Those With Ostium Secundum Atrial Septal Defects, J. Clin. Ultrasound, 7: 345-348 (1979).
Rossignol, et al., Left-to-Right Atrial Shunting: New Hope for Heart Failure, www.thelancet.com, 387:1253-1255 (2016).
Roven., Effect of Compromising Right Ventricular Function in Left Ventricular Failure by Means of Interatrial and Other Shunts 24:209-219 (Aug. 1969).
Salehian, et al., Improvements in Cardiac Form and Function After Transcatheter Closure of Secundum Atrial Septal Defects, Journal of the American College of Cardiology, 45(4):499-504 (2005).
Schmitto, et al., Chronic Heart Failure Induced by Multiple Sequential Coronary Microembolization in sheep, The International Journal of Artificial Organs, 31(4):348-353 (2008).
Schubert, et al., Left ventricular Conditioning in the Elderly Patient to Prevent Congestive Heart Failure After Transcatheter Closure of the Atrial Septal Defect, Catheterization and Cardiovascular Interventions, 64(3): 333-337 (2005).
Stormer, et al., Comparative Study of in Vitro Flow Characteristics Between a Human Aortic Valve and a Designed Aortic Valve and Six Corresponding Types of Prosthetic Heart Valves, European Surgical Research 8(2): 117-131 (1976).
Stumper, et al., Modified Technique of Stent Fenestration of the Atrial Septum, Heart, 89:1227-1230, (2003).
Supplementary European Search Report dated Nov. 13, 2009 in EP Patent Appl. Serial No. 05703174.2. (0430).
Trainor, et al., Comparative Pathology of an Implantable Left Atrial Pressure Sensor, ASAIO Journal, Clinical Cardiovascular/Cardiopulmonary Bypass, 59(5):486-492 (2013).
Written Opinion of the International Searching Authority dated Apr. 7, 2008 received from the Patent Cooperation Treaty Re.: Application No. PCT/IL05/00131 (0410).
Zhou, et al., Unidirectional Valve Patch for Repair of Cardiac Septal Defects with Pulmonary Hypertension, Annals of Thoracic Surgeons, 60:1245-1249, (1995).
Abraham et al., "Hemodynamic Monitoring in Advanced Heart Failure: Results from the LAPTOP-HF Trial," J Card Failure, 22:940 (2016) (Abstract Only).
Abraham et al., "Sustained efficacy of pulmonary artery pressure to guide adjustment of chronic heart failure therapy: complete follow-up results from the Champion randomised trial," The Lancet, doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).
Abreu et al., "Doppler ultrasonography of the femoropopliteal segment in patients with venous ulcer," J Vasc Bras., 11(4):277-285 (2012).
Adamson et al., "Ongoing Right Ventricular Hemodynamics in Heart Failure Clinical Value of Measurements Derived From an Implantable Monitoring System," J Am Coll Cardiol., 41(4):565-571 (2003).
Adamson et al., "Wireless Pulmonary Artery Pressure Monitoring Guides Management to Reduce Decompensation in Heart Failure With Preserved Ejection Fraction," Circ Heart Fail., 7:935-944 (2014).
Ambrosy et al. "The Global Health and Economic Burden of Hospitalizations for Heart Failure," J Am Coll Cardiol., 63:1123-1133 (2014).
Aminde et al., "Current diagnostic and treatment strategies for Lutembacher syndrome: the pivotal role of echocardiography," Cardiovasc Diagn Ther., 5(2):122-132 (2015).
Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).
Anderas et al., "Tilted c-axis Thin-Film Bulk Wave Resonant Pressure Sensors with Improved Sensitivity," IEEE Sensors J., 12(8):2653-2654 (2012).
Ataya et al., "A Review of Targeted Pulmonary Arterial Hypertension-Specific Pharmacotherapy," J. Clin. Med., 5(12):114 (2016).
Bannan et al., "Characteristics of Adult Patients with Atrial Septal Defects Presenting with Paradoxical Embolism.," Catheterization and Cardiovascular Interventions, 74:1066-1069 (2009).
Baumgartner et al., "ESC Guidelines for the management of grown-up congenital heart disease (new version 2010)—The Task Force on

(56) References Cited

OTHER PUBLICATIONS the Management of Grown-up Congenital Heart Disease of the European Society of Cardiology (ESC)," Eur Heart J., 31:2915-2957 (2010).
Beemath et al., "Pulmonary Embolism as a Cause of Death in Adults Who Died With Heart Failure," Am J Cardiol., 98:1073-1075 (2006).
Benza et al., "Monitoring Pulmonary Arterial Hypertension Using an Implantable Hemodynamic Sensor," Chest, 156(6):1176-1186 (2019).
Borlaug, et al., Latent Pulmonary Vascular Disease May Alter The Response to Therapeutic Atrial Shunt Device in Heart Failure, Circulation (Mar. 2022).
Bruch et al., "Fenestrated Occluders for Treatment of ASD in Elderly Patients with Pulmonary Hypertension and/or Right Heart Failure," J Interven Cardiol., 21(1):44-49 (2008).
Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Davies et al., "Abnormal left heart function after operation for atrial septal defect," British Heart Journal, 32:747-753 (1970).
Della Lucia et al., "Design, fabrication and characterization of SAW pressure sensors for offshore oil and gas exploration," Sensors and Actuators A: Physical, 222:322-328 (2015).
Drazner et al., "Prognostic Importance of Elevated Jugular Venous Pressure and a Third Heart Sound in Patients with Heart Failure," N Engl J Med., 345(8):574-81 (2001).
Drazner et al., "Relationship between Right and Left-Sided Filling Pressures in 1000 Patients with Advanced Heart Failure," Heart Lung Transplant, 18:1126-1132 (1999).
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eshaghian et al., "Relation of Loop Diuretic Dose to Mortality in Advanced Heart Failure," Am J Cardiol., 97:1759-1764 (2006).
Feldman et al., "Transcatheter Interatrial Shunt Device for the Treatment of Heart Failure with Preserved Ejection Fraction (Reduce LAP-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).
Flachskampf, et al., Influence of Orifice Geometry and Flow Rate on Effective Valve Area: An In Vitro Study, Journal of the American College of Cardiology, 15(5):1173-1180 (Apr. 1990).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for In-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geva et al., "Atrial septal defects," Lancet, 383:1921-32 (2014).
Gheorghiade et al., "Acute Heart Failure Syndromes, Current State and Framework for Future Research," Circulation, 112:3958-3968 (2005).
Gheorghiade et al., "Effects of Tolvaptan, a Vasopressin Antagonist, in Patients Hospitalized With Worsening Heart Failure A Randomized Controlled Trial," JAMA., 291:1963-1971 (2004).
Go et al. "Heart Disease and Stroke Statistics—2014 Update—A Report From the American Heart Association," Circulation, 128:1-267 (2014).
Guillevin et al., "Understanding the impact of pulmonary arterial hypertension on patients' and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France—Results from a National Registry," Am J Respir Crit Care Med., 173:1023-1030 (2006).
International Search Report & Written Opinion dated Feb. 9, 2022 in Int'l PCT Patent Appl. Serial No. PCT/IB2021/060473 (2010).
International Search Report & Written Opinion dated May 17, 2022 in Int'l PCT Patent Appl. Serial No. PCT/IB2022/051177 (2310).
International Search Report & Written Opinion dated Jul. 14, 2020 in Int'l PCT Patent Appl. Serial No. PCT/IB2020/053832 (1210).
International Search Report & Written Opinion dated Jul. 20, 2020 in Int'l PCT Patent Appl. Serial No. PCT/IB2020/054699 (1710).
International Search Report & Written Opinion dated Jul. 23, 2021 in Int'l PCT Patent Appl. Serial No. PCT/IB2021/053594 (1910).

(56) References Cited

OTHER PUBLICATIONS

International Search Report & Written Opinion dated Aug. 12, 2020 in Int'l PCT Patent Appl. Serial No. PCT/IB2020/053118 (1010).
International Search Report & Written Opinion dated Sep. 21, 2020 in Int'l PCT Patent Appl. Serial No. PCT/IB2020/054306 (1510).
Jessup et al. "2009Focused Update: ACC/AHA Guidelines for the Diagnosis and Management of Heart Failure in Adults: A Report of the American College of Cardiology Foundation/American Heart Association Task Force on Practice Guidelines: Developed in Collaboration With the International Society for Heart and Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Kaye, et al., One-Year Outcomes After Transcatheter Insertion of an Interatrial Shunt Device for the Management of Heart Failure with Preserved Ejection Fraction, Circulation: Heart Failure, 9(12):e003662 (Dec. 2016).
Keogh et al., "Interventional and Surgical Modalities of Treatment in Pulmonary Hypertension," J Am Coll Cardiol., 54:S67-77 (2009).
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lammers et al., "Efficacy and Long-Term Patency of Fenerstrated Amplatzer Devices in Children," Catheter Cardiovasc Interv., 70:578-584 (2007).
Lindenfeld et al. "Executive Summary: HFSA 2010 Comprehensive Heart Failure Practice Guideline," J. Cardiac Failure, 16(6):475-539 (2010).
Luo, Yi, *Selective and Regulated RF Heating of Stent Toward Endohyperthermia Treatment of In-Stent Restenosis*, A Thesis Submitted in Partial Fulfillment of The Requirements For The Degree of Master of Applied Science in The Faculty of Graduate and Postdoctoral Studies (Electrical and Computer Engineering), The University of British Columbia, Vancouver, Dec. 2014.
MacDonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," Journal of Cardiac Failure., 21(6): 479-488 (2015).
McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).

McLaughlin et al., "Survival in Primary Pulmonary Hypertension—The Impact of Epoprostenol Therapy.," Circulation, 106:1477-1482 (2002).
Mu et al., "Dual mode acoustic wave sensor for precise pressure reading," Applied Physics Letters, 105:113507-1-113507-5 (2014).
Nagaraju et al., "A 400μW Differential FBAR Sensor Interface IC with digital readout," IEEE., pp. 218-221 (2015).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," Pace, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin. 2018.07.001 (2018).
Ross et al., "Interatrial Communication and Left Atrial Hypertension—A Cause of Continuous Murmur," Circulation, 28:853-860 (1963).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schneider et al., "Fate of a Modified Fenestration of Atrial Septal Occluder Device after Transcatheter Closure of Atrial Septal Defects in Elderly Patients," J Interven Cardiol., 24:485-490 (2011).

(56) References Cited

OTHER PUBLICATIONS

Scholl et al., "Surface Acoustic Wave Devices for Sensor Applications," Phys Status Solidi Appl Res., 185(1):47-58 (2001) (Abstract Only).
Setoguchi et al., "Repeated hospitalizations predict mortality in the community population with heart failure," Am Heart J., 154:260-266 (2007).
Shah, et al., Atrial Shunt Device For Heart Failure With Preserved And Mildly Reduced Ejection Fraction (Reduce LAP-HF II): A Randomised, Multicentre, Blinded, Sham-Controlled Trial, The Lancet, 399(10330):1130-1140 (Mar. 2022).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce LAP-HF I) Trial—A Randomized Clinical Trial," JAMA Cardiol. doi:10.1001/jamacardio.2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Su et al., "A film bulk acoustic resonator pressure sensor based on lateral field excitation," International Journal of Distributed Sensor Networks, 14(11):1-8 (2018).
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).
Vank-Noordegraaf et al., "Right Heart Adaptation to Pulmonary Arterial Hypertension—Physiology and Pathobiology," J Am Coll Cardiol., 62(25):D22-33 (2013).
Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).
Wang et al., "Tire Pressure Monitoring System and Wireless Passive Surface Acoustic Wave Sensor," Appl Mech Mater., 536(537):333-337 (2014).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).
Zhang et al., "Film bulk acoustic resonator-based high-performance pressure sensor integrated with temperature control system," J Micromech Microeng., 27(4):1-10 (2017).
Clowes, et al., Mechanisms of Arterial Graft Healing—Rapid Transmural Capillary Ingrowth Provides a Source of Intimal Endothelium and Smooth Muscle in Porous PTFE Prostheses, Am. J. Pathol., 123(2):220-230 (May 1986).
Greitz, et al., Pulsatile Brain Movement and Associated Hydrodynamics Studied by Magnetic Resonance Phase Imaging, Diagnostic Neuroradiology, 34(5): 370-380 (1992).
International Search Report & Written Opinion dated Feb. 3, 2023 in Int'l PCT Patent Appl. Serial No. PCT/IB2022/060621 (2210).
International Search Report & Written Opinion dated Mar. 29, 2023 in Int'l PCT Patent Appl. Serial No. PCT/IB2023/050743 (2410).

* cited by examiner

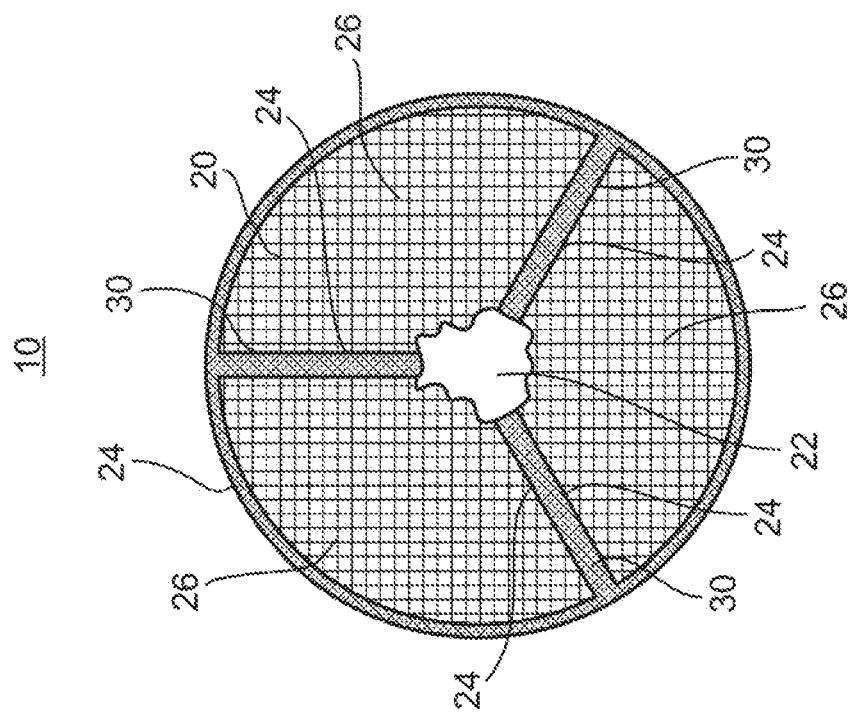
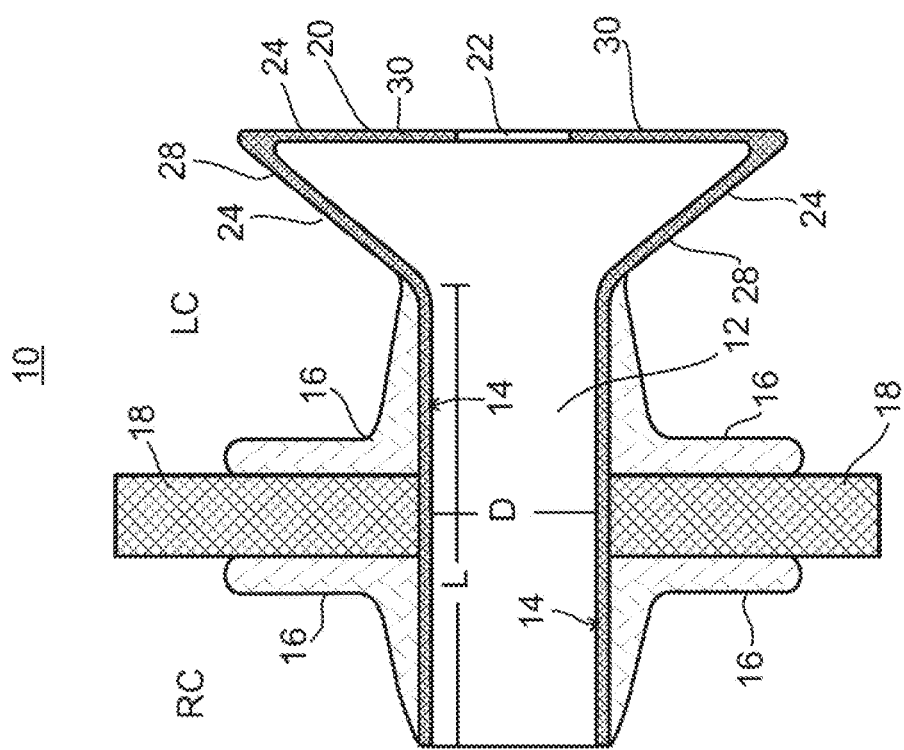

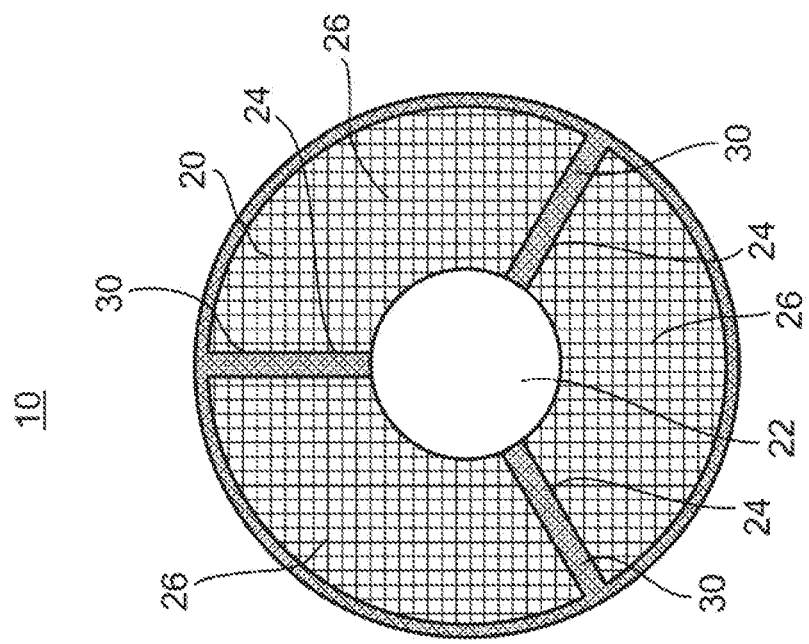
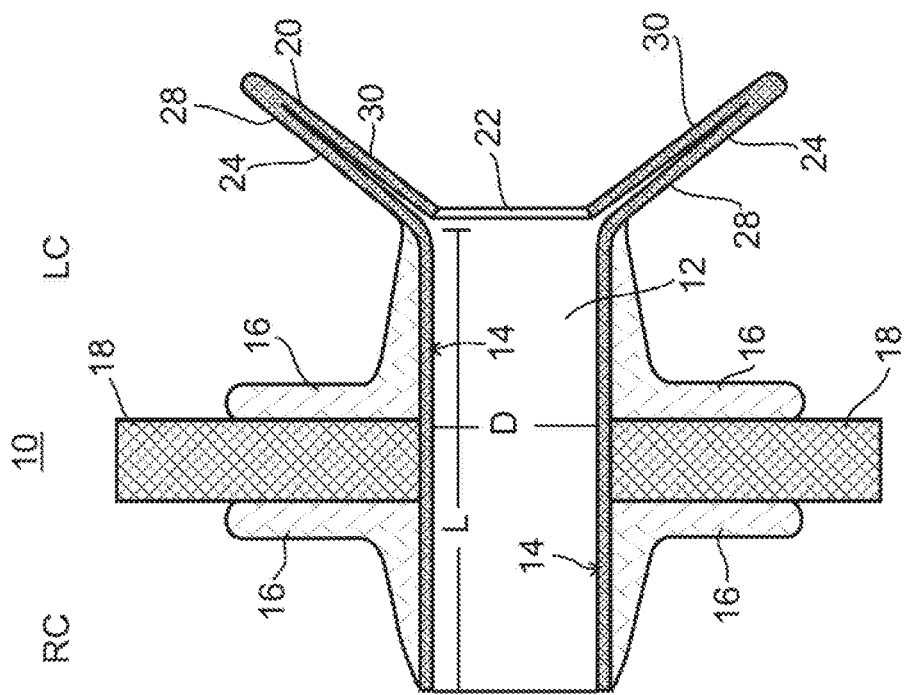

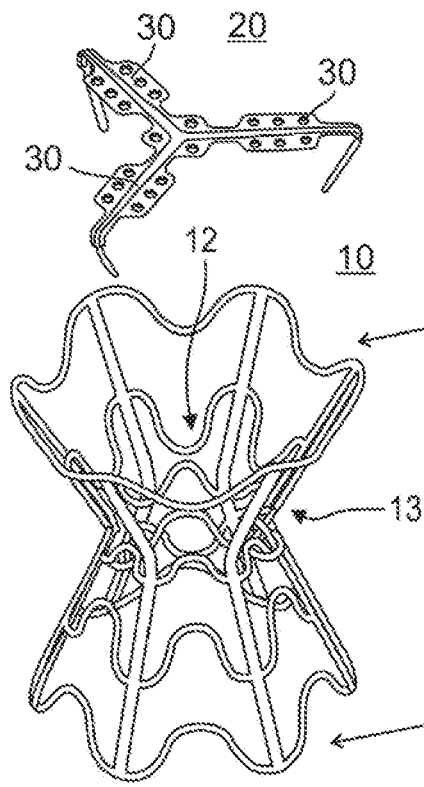 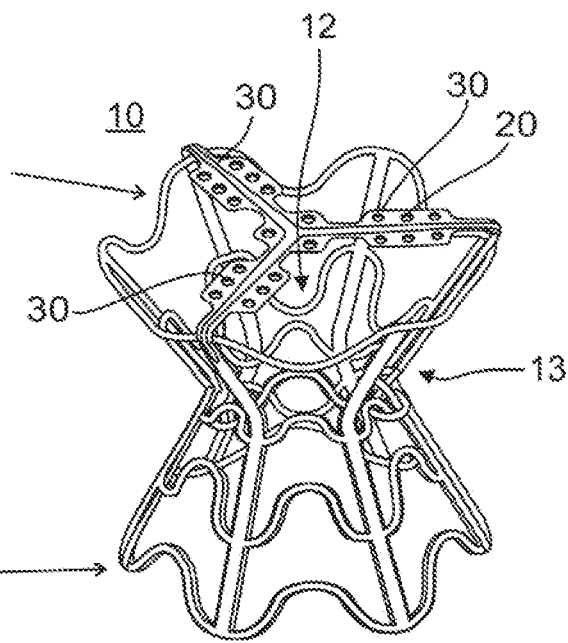
FIG. 5A  FIG. 5B
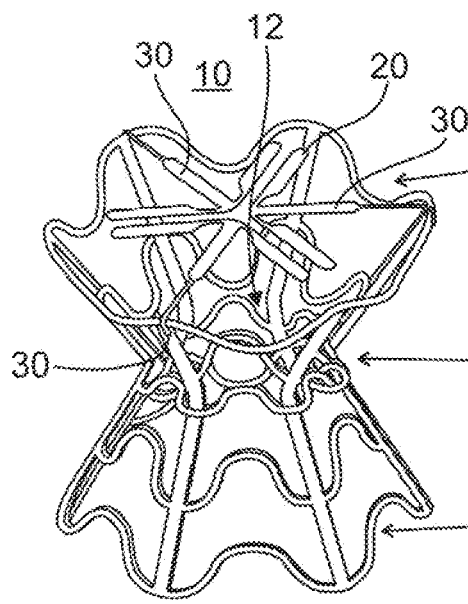 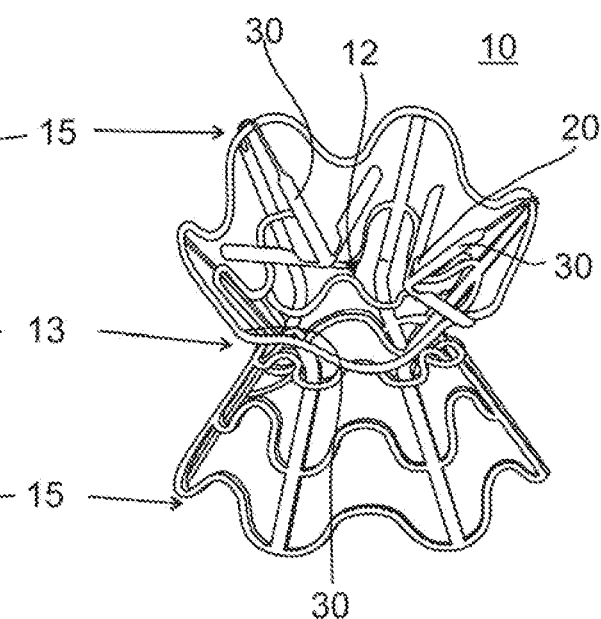
FIG. 5C  FIG. 5D

DEVICE AND METHOD FOR REGULATING PRESSURE IN A HEART CHAMBER

CROSS-REFERENCE TO RELATED APPLICATIONS

This application is a continuation of U.S. patent application Ser. No. 15/650,783, filed Jul. 14, 2017, now U.S. Pat. No. 10,639,459, which is a divisional application of U.S. patent application Ser. No. 14/227,982, filed Mar. 27, 2014, now U.S. Pat. No. 9,707,382, which is a continuation under 35 U.S.C. § 120 of U.S. patent application Ser. No. 13/108,880, filed May 16, 2011, now U.S. Pat. No. 8,696,611, which is a continuation under 35 U.S.C. § 120 of International Patent Application No. PCT/IL2010/000354, filed May 4, 2010 and entitled "Device and Method for Regulating Pressure in a Heart Chamber," which claims the benefit of U.S. Provisional Patent Application No. 61/175,073, filed May 4, 2009, and U.S. Provisional Patent Application No. 61/240,667, filed Sep. 9, 2009, the entire contents of each of which are incorporated by reference herein.

FIELD

The present invention relates to a device which can be used to regulate pressure in a heart chamber. Specifically, the present invention relates to a device which can be used to lower a blood pressure in a left atrium in response to an increase in left atrial pressure and to a method of utilizing such a device in treatment of congestive heart failure related conditions such as Pulmonary Edema and decompensated heart failure caused by elevated pressures in a left side chamber of a heart.

BACKGROUND OF THE INVENTION

Congestive heart failure (CHF) is a condition in which the blood pumping function of the heart is inadequate to meet the needs of body tissue. CHF is one of the most common causes of hospitalization and mortality in Western society.

CHF results from a weakening or stiffening of the heart muscle most commonly caused by myocardial ischemia (due to, for example, myocardial infarction) or cardiomyopathy (e.g. myocarditis, amyloidosis). Such weakening or stiffening leads to reduced cardiac output, an increase in cardiac filling pressures, and fluid accumulation. Congestive heart failure (CHF) is generally classified as systolic heart failure (SHF) or diastolic heart failure (DHF).

In SHF, the pumping action of the heart is reduced or weakened. A common clinical measurement is the ejection fraction (EF) which is a function of the volume of blood ejected out of the left ventricle (stroke volume), divided by the maximum volume remaining in the left ventricle at the end of diastole or relaxation phase. A normal ejection fraction is greater than 50%. Systolic heart failure has a decreased ejection fraction of less than 50%. A patient with SHF may usually have a larger left ventricle because of phenomena called cardiac remodeling aimed to maintain adequate stroke-volume. This pathophysiological mechanism is associated with increased atrial pressure and left ventricular filling pressure.

In DHF, the heart can contract normally but is stiff, or less compliant, when it is relaxing and filling with blood. This impedes blood filling into the heart and produces backup into the lungs resulting in pulmonary venous hypertension and lung edema. Diastolic heart failure is more common in patients older than 75 years, especially in women with high blood pressure. In diastolic heart failure, the ejection fraction is normal.

CHF can be managed via a pharmacological approach which utilizes vasodilators for reducing the workload of the heart by reducing systemic vascular resistance and/or diuretics which prevent fluid accumulation and edema formation, and reduce cardiac filling pressure.

In more severe cases of CHF, assist devices, such as mechanical pumps can be used to reduce the load on the heart by performing all or part of the pumping function normally done by the heart. Temporary assist devices and intra-aortic balloons may be helpful. Cardiac transplantation and chronic left ventricular assist device (LVAD) implants may often be used as last resort. However, all the assist devices currently used are intended for improving pumping capacity of the heart and increasing cardiac output to levels compatible with normal life and are typically used to sustain the patient while a donor heart for transplantation becomes available. There are also a number of pacing devices used to treat CHF. Mechanical devices enable propulsion of significant amounts of blood (liters/min) but are limited by a need for a power supply, relatively large pumps and possibility of hemolysis and infection are all of concern.

Surgical approaches such as dynamic cardiomyoplasty or the Batista partial left ventriculectomy are used in severe cases, as is heart transplantation, although the latter is highly invasive and limited by the availability of donor hearts.

Although present treatment approaches can be used to manage CHF, there remains a need for a device for treating CHF which is devoid of the above described limitations of prior art devices.

SUMMARY OF THE INVENTION

According to one aspect of the present invention there is provided device for regulating blood pressure in a heart chamber comprising a shunt being positionable across the septum of the heart, specifically in the fossa ovalis, the shunt being for enabling blood flow between a left heart chamber and a right heart chamber, wherein a flow rate capacity of the device is a function of pressure difference between the left atrium and the right atrium.

In congestive heart failure the elevation in the left atrial pressure is higher than the elevation in the right atrial pressure and therefore the flow rate capacity is mainly regulated by the left atrial pressure changes.

In left heart failure, elevation of right heart pressure is also a function of left heart pressure. When the left atrium pressure rises neuro-hormonal compensatory mechanisms cause more endothelin secretion and less NO. This mechanism constricts the blood vessels and raises the right pulmonary artery pressure. If it wouldn't have occurred there would have been no flow across the pulmonary circulation. Therefore even though the flow across the present device is solely dependent on the pressure gradient between the left and right atrium it is correct to assume that its all a function of the left atrium pressure.

According to further features in preferred embodiments of the invention described below, the flow rate capacity of the device increases by 0.1-1.5 L/min when the average pressure in the left heart chamber is greater than 20 mmHg.

According to still further features in the described preferred embodiments the flow rate capacity of the device is 0.1-0.3 l/min when the average pressure in the left heart chamber is less than 20 mmHg.

According to still further features in the described preferred embodiments the device further comprises a valve for regulating flow through the shunt, wherein the valve increases a flow rate capacity of the device in response to an increase in pressure in the left heart chamber thus creating an increase in the differential pressure between the left and the right atria.

According to still further features in the described preferred embodiments the valve is a tissue valve.

According to still further features in the described preferred embodiments the tissue valve is a pericardium tissue valve.

According to still further features in the described preferred embodiments the pericardium tissue is derived from a Porcine, Equine, or Bovine source.

According to still further features in the described preferred embodiments a fluid conduit of the shunt increases in cross section area with the increase in pressure in the left heart chamber According to still further features in the described preferred embodiments the device further comprises anchoring elements for attaching the device to the septum.

According to still further features in the described preferred embodiments the device further comprises anchoring elements for attaching the device to the septum.

According to still further features in the described preferred embodiments the device is diabolo-shaped such that the device only contacts tissue forming the opening in the septum and not tissue surrounding the opening.

According to still further features in the described preferred embodiments the diabolo shape does not allow migration of the valve through the septum.

According to another aspect of the present invention there is provided a method of assessing the hemodynamic condition of a subject comprising implanting the present device in the subject and determining flow through, or valve leaflet angle of, the device, the flow through or leaflet angle being indicative of left atrial pressure.

According to still further features in the described preferred embodiments, determining is effected via an imaging approach such as ultrasound, fluoroscopy, MRI and the like.

The present invention successfully addresses the shortcomings of the presently known configurations by providing a device which can more accurately compensate for a disordered hemodynamic state of a heart of a CHF patient and which can be implanted using minimally invasive approaches.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-B illustrate a side view (FIG. 1A) and a frontal view (FIG. 1B) of a device for regulating pressure in a heart chamber constructed according to one embodiment the present invention and showing the valve component in the closed position.

FIGS. 2A-B illustrate a side view (FIG. 2A) and a frontal view (FIG. 2B) of the device of FIGS. 1A-B showing the valve component in the open position.

FIG. 5A-D illustrate isometric views of a diabolo shaped device of the present invention. FIG. 5A separately illustrates the device body and valve substructures, while FIGS. 5B-5D illustrate the assembled device. The valve is shown in a closed position in FIGS. 5B-SC, and in an open position in FIG. 5D.

DETAILED DESCRIPTION

Figure 3:
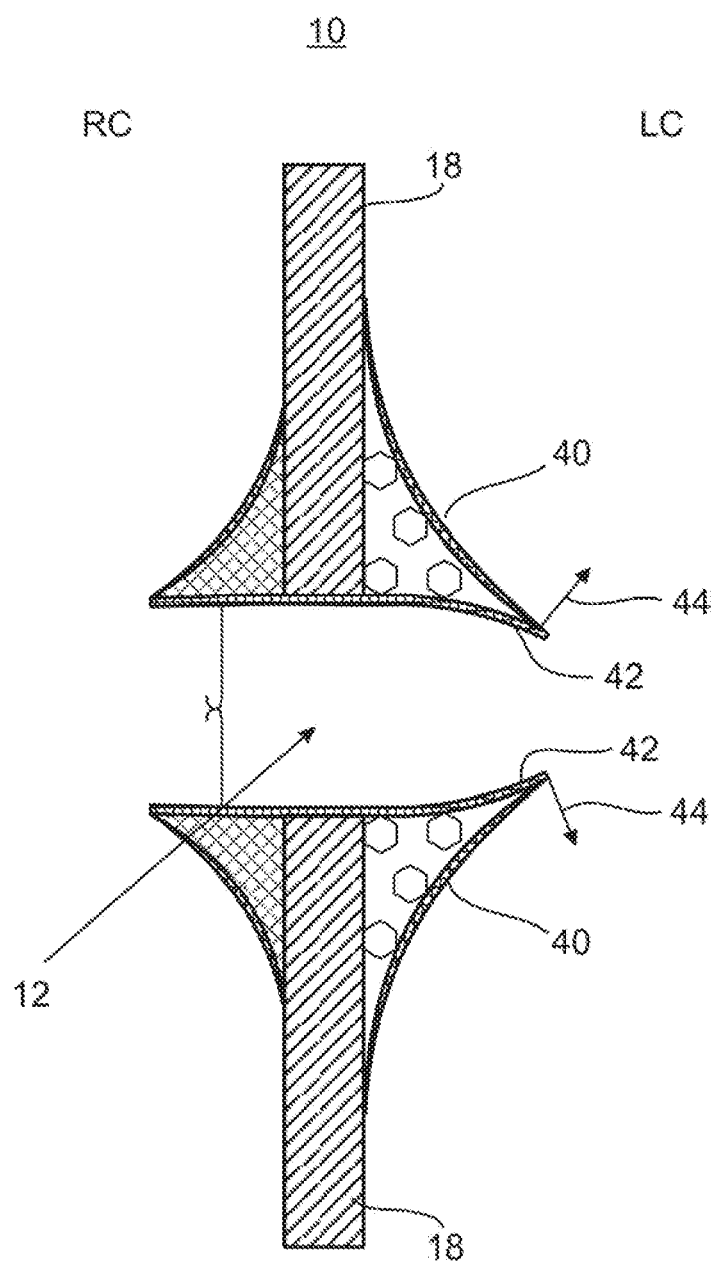
FIG. 3 illustrates a side view of a device for regulating pressure in a heart chamber constructed according to another embodiment the present invention.

The present invention is of a device and method which can be used to regulate pressure in a heart chamber. Specifically, the present invention can be used to treat elevated chamber pressures present in a patient suffering from CHF or having a Patent Foremen Ovale (PFO) or an Atrial Septal Defect (ASD) that requires repair and prevention of embolization from right to left atriums but is preferably left with residual flow between atriums so as not to traumatize heart hemodynamics.

The present device can also be used to determine the pressure in the left atrium and thus assist in defining the exact clinical condition of the patient which can be used to alter/adjust patient medication and help stabilize hemodynamics.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

CHF is one of the most common causes of hospitalization and mortality in Western society. At present, CHF is treated using pharmaceutical, mechanical or surgical approaches.

In an attempt to traverse the limitations of prior art approaches. Applicant has devised a novel minimally invasive approach for reducing the disordered hemodynamics associated with CHF. Such an approach, which is described in US 20020173742 and 20070282157, the entire contents of each of which are incorporated herein by reference, utilizes a device which includes a shunt which is positioned between heart atria and enables blood flow between the left and right atria. The device includes an adjustable flow regulation mechanism which is configured for regulating the flow of blood through the shunt in relation to a pressure differential between the chambers.

While reducing the present invention to practice, the present inventors have continued to experiment and model this approach and have surprisingly discovered that disorders or conditions which result from abnormal heart hemodynamics, such as those characterizing CHF, can be treated by regulating blood flow between heart chambers mostly as a function of left chamber pressure.

Thus according to one aspect of the present invention there is provided a device for regulating blood pressure in a heart chamber, such as a ventricle or an atria.

As is further described hereinbelow, the present device can be used in human subjects suffering from CHF as well as in subjects which have septal defects but are not candidates for complete septal closure.

The device includes a shunt which preferably includes a valve for controlling flow through the shunt. The device is positionable within a septum of the heart and is configured for enabling blood flow between a left heart chamber and a right heart chamber. The device is configured such that a flow rate capacity thereof is a function of (blood) pressure gradient between the left and right atria. Because the right atria pressure is mostly affected from the left atria pressure, flow regulation is mainly governed by the left atria pressure.

In a normal heart, beating at around 70 bpm, the stroke volume needed to maintain normal CO (Cardiac output) is between 60 ml-100 ml. When the preload, after-load and contractility are normal, the pressures needed to achieve this CO values are as described in Table 1 below. In CHF the Hemodynamic parameters change (Table 1) because in order to maximize CO the heart needs higher pressures to either overcome the higher after-load or lower contractility or damaged preload.

TABLE 1

Ranges of heart parameters in normal and CHF heart

| Parameter | Normal Range | CHF Range |
|---|---|---|
| Right Atrial Pressure (RAP) | 2-6 mmHg | 6-15 mmHg |
| Right Ventricular Pressure (RVP) | 15-25 mmHg | 20-40 mmHg |
| Left Atrial Pressure (LAP) | 6-12 mmHg | 15-30 mmHg |
| Left Ventricular Pressure | 6-120 mmHg | 20-220 mmHg |
| Cardiac Output (CO) | 4.0-8.0 l/min | 2-6 l/min |
| Stroke Volume (SV) | 60-100 ml/beat | 30-80 ml/beat |

Thus, reduction of left chamber blood pressure, and in particular left atrial pressure (LAP), can be used to offset abnormal hemodynamics characterizing CHF and other heart pathologies and thereby treat conditions associated therewith. For example, the present invention can be used to treat pulmonary edema associated with CHF. Pulmonary edema, which is the most severe manifestation of CHF, develops when an imbalance in the heart pumping function causes an increase in lung fluid secondary to leakage from pulmonary capillaries into the interstitium and alveoli of the lung.

As is described in detail in Example 1 of the Examples section which follows, the present device can be used to alleviate such an imbalance by regulating flow from the left atrium to the right atrium (through a septum). The flow capacity of the present device changes mainly due to changes in left atrial pressure and as a result, flow from the left atrium to the right atrium is mainly a function of the left atrial pressure.

The insight gained by the present inventors from experimenting with various device configurations and modeling blood flow between heart chambers, has led to the formulation of several design parameters:

(i) Changes in left chamber pressure directly affect flow capacity (thus volume) through the device thereby resulting in LA decompression and prevention of pulmonary congestion.

(ii) In situation where peak left chamber pressure exceeds a predetermined amount, pressure is lowered by increased flow capacity in the device, for example, in cases where LAP exceeds 25 mmHg, increased flow capacity decreases LAP by 3-6 mmHg.

(iii) The flow capacity of the present device gradually changes starting at left atrial pressure (LAP) of about 15 mmHg and reaches full capacity at an LAP of 25 mmHg. The device can be designed with characteristics that are patient dependent i.e. if a patient is screened and found to be at pulmonary Edema risk at 20 mmHg then the device is configured for reaching full flow capacity at 20 mmHg.

(iv) The flow capacity of the present device starts to change when the pressure gradient across the septum is between 5 mmHg-10 mmHg. Up to 5 mmhg the valve of the present device remains substantially closed. Between 5-10 mmHg the valve slightly opens and flow of up to 0.5 l/min is supported. At gradients between 10-20 mmHg the flow across the valve rapidly increases as a function of the opening of the leaflets. The flow reaches 1.5 l/min at 20 mmHg. Above 20 mmHg the valve is fully open and the flow is defined by the narrow part of the lumen of the device (in the diabolo configuration, the narrow portion can be between 4-6 mm depending on the configuration).

(v) The device is patient specific i.e. in patients where the pressure gradients are very high the valve will be built such that the min opening gradient will be higher than in those patients where the gradients are lower. For example: if the patient has a mean LA gradient of 16 mmHg and mean RA pressure of 8 mmhg the valve will be assembled with the parameters described in (iv). If however, the mean LA pressure is 23 mmHg and the mean RA pressure is 8 mmHg the minimal valve opening will be at 10 mmhg and full opening will only occur at the 25 mmHg gradient.

(vi) The device is designed to allow constant flow regardless of left chamber pressure to maintain its patency over time. Constant flow refers to a flow during each heart cycle. However in each cycle, if the mean left atrial pressure is below 20 mmHg, flow will only occur during the V-Wave of the atria. The V-Wave of the atria occurs at the end of the atria's diastole. CHF patients, especially those having mitral regurgitation, have V-Waves characterized by very high pressure that can reach up to 40 mmHg for up to 150 ms of each heart beat. The rest of the cycle the left atrium pressure drops. In such patients, the present device will enable flow that maintains the patency of the device only for a short duration (less than 15%) of each cycle, and thus the flow across the valve of the present device will be less than 0.3 L/min and there will be negligible effect on the cardiac output.

(vii) A diameter of a shunt (conduit) of the device changes from 0-6 mm as a function of the pressure changes to prevent large volume flow when left chamber pressure is below a predetermined threshold (e.g. when LAP is below 25 mmHg).

(viii) The device is configured to prevent right chamber blood from entering the left chamber under elevated right chamber pressure conditions where RAP is higher than LAP. Selecting a shunt length of above 10 mm prevents RA blood from reaching the Left Atrium also during onset of slightly higher RA-LA pressure gradient. Another feature that disables right to left shunting is the valve that is normally closed when pressures in the right atrium are slightly higher than in the left atrium. In CHF caused by left heart failure there are almost no cases where there is a higher right atrium pressure. Therefore prevention of flow in pressures gradients of less than 5 mmHg eliminates the risk of right to left shunting in CHF patients.

(ix) When left chamber pressure is below a predetermined threshold (e.g. below 25 mmHg in the LA), the device is designed to minimize CO reduction to less than 0.1 l/min.

(x) A reduced flow capacity under pressures that are below a predetermined threshold ensures that the device prevents RV overload, and maintains Qp/Qs<1.3.

(xi) The Device can also be designed to allow controlled tissue growth (up to 1 mm thickness) to become inert over time but not to lead to occlusion by excessive growth in or around the shunt.

To enable such functionality, the present device is an intra-septal implant which is attached to a septum separating two heart chambers (e.g. left atria from right atria or left ventricle from right ventricle). The device includes a shunt and optionally a valve having an opening capable of changing its diameter mainly as a function of the left chamber pressure.

The present device is preferably designed having a 5 mm opening diameter following implantation and tissue ingrowths. The device is configured for maintaining constant flow through the V-wave portion of each heart cycle at about 0.1-0.3 l/min. The maximum opening diameter of the shunt/valve is preferably 5 mm to enable an approximate maximum flow capacity of 1.5 l/min.

The device of the present invention or a portion thereof (e.g. valve) is preferably constructed from a laser cut tube to a shape of a stent, covered by ePTFE to create a shunt and a tissue valve at the left atria's end (Pericardium equine, Bovine, Porcine between 0.1 mm-0.5 mm tissue thickness) which is sutured or welded to the frame. To enable percutaneous delivery, the present device can preferably be collapsed to an overall diameter of less than 15F Embodiments of the device of the present invention suitable for use in regulating left atrial pressure are illustrated in FIGS. 1a-3. It will be appreciated that although the following describes use of the present device in regulating LAP, alternative uses in regulating LVP, RAP or RVP are also envisaged by the present inventors.

FIGS. 1A-1B illustrate one embodiment of the present device which is referred to herein as device 10. FIGS. 1A-1B illustrate a cross sectional view (FIG. 1A) or a frontal view (FIG. 1B) of device 10 in a configuration in which flow capacity is at a minimum.

Device 10 includes a shunt 12 which serves as a conduit for blood flow between a left chamber (LC) and a right chamber (RC). Shunt 12 is configured as a tube having a diameter (D) selected from a range of 3-10 mm. Shunt 12 can be constructed from a polymer such as silicone, ePTFE, or Dacron via extrusion or molding or from an alloy (e.g. titanium, NITINOL, Cobalt Chromium and the like). It can also be constructed from tissue derived from vein grafts or pericardium. In any case, shunt 12 preferably includes a tissue outer structure and potentially an inner polymer cover. The tubular frame of shunt 12 can be constructed by cutting a tube or by wrapping a wire over a mandrel and covering the resultant tubular structure with animal tissue (e.g. pericardium derived from bovine, equine or porcine tissue), PTFE or Dacron which is sutured or welded to the frame. Since walls 14 contact blood as it flows through shunt 12, such walls can be coated or impregnated with carbon, heparin and endothelial cells. Such coating can be used to reduce drag and prevent blood coagulation and formation of clots and to promote controlled tissue growth. Alternatively, walls 14 can be textured or provided with fine electropolished smooth metal surfaces in order to increase laminar flow and decrease turbulence.

Shunt 12 is selected having a length (L) of 10-20 mm and a wall 14 thickness of 0.1-0.5 mm.

Device 10 further includes anchoring elements 16 which serve to anchor shunt 12 to septum 18. Anchoring elements are designed for anchoring septal tissue. The device will be implanted in the septum preferably in the Fossa Ovalis were the wall thickness is between 0.2-1 mm. In that respect, septal anchoring is preferably effected by expanding the diameter of shunt 12 at least 2 mm larger than the Transeptal puncture diameter used for implantation. This expansion will give the radial stiffness needed to hold the implant in place. Furthermore anchoring elements 16 are configured for applying axial pressure against the septum to thereby add friction that will prevent relative movement between device 10 and the septum. Such pressure is achieved by the shape of device 10 when in position. Anchoring elements 16 can be constructed from a NITINOL wire mesh or a Polymer (e.g. Dacron, ePTFE) sutured to the wire. Anchoring elements 16 are configured with an elastic force directed towards each other such that when device 10 is positioned, anchoring elements 16 apply opposing inward forces to the septal tissue.

Since implantation of device 10 within the septum will lead to tissue growth around device 10 in response to injury, anchoring elements 16 and shunt 12 are designed to compensate for such tissue growth. For example, device 10 or any of its components can be seeded with endothelial cells or coated with heparin or impregnated with carbon in order to controlled tissue growth and prevent clot formation.

Shunt 12 is designed such that tissue ingrowth will not be excessive. Ends of shunt 12 protrude from the septal plane to minimize rapid tissue growth. Device 10 is also designed to minimize an effect on atrial flow in order not to cause hemolysis. In that respect, ends of shunt 12 do not protrude by more than 7 mm into opposing Atria and in addition the surfaces of shunt 12 exposed to flow are preferably rounded.

In the embodiment shown in FIGS. 1A-2B, device 10 also includes a valve 20 which functions in regulating flow through shunt 12. In this embodiment, the flow capacity of shunt 12 is fixed, however, flow therethrough is regulated by a diameter of opening 22 of valve 20 and as such the overall flow capacity of device 10 falls within a preset range (e.g. 0.2-1.5 l/min).

Valve 20 can be constructed having any configuration capable of supporting baseline (minimal) flow when in a closed position (Shown in FIGS. 1A-1B) while being capable of a gradual or binary response to left chamber pressure which exceeds a predetermined threshold (e.g. above 25 mmHg in left atrium). Valve 20 includes a frame 24 which is constructed from a polymer or an alloy (e.g. NITINOL) with overstretched polymer or tissue (as described above for shunt 12). Valve 20 can be attached to shunt 12 or constructed as an extension thereof (contiguous).

Construction of device 10 of FIGS. 1A-2B is described in detail in Example 2 of the Examples section which follows.

Opening 22 in valve 20 is formed in front wall 26 of valve 20. In the case of valve 20 constructed from frame 24 and covering of a polymeric material or tissue, opening 22 can be constructed by overlapping leaflets of polymer or tissue. The valve can be cut from one or three leaflets that are sutured or welded to their commisures in the closed position of the valve thus leaving a slack that once stretched leads to enlargement of opening 22.

A binary response configuration of valve 20 assumes one of two states, a closed state (FIGS. 1a-b) which supports flow of 0.1-0.5 l/min or an open state (FIGS. 2A-2B) which supports flow of 0.5-1.2 l/min. Such a binary configuration can be constructed by, for example, designing frame 24 to be capable of assuming one of two states in response to pressure applied to front (26) or side (28) walls of valve 20. The frame of valve 20 includes NITINOL commisures that under predetermined forces (few grams) are able to rotate inwards. This is achieved by a designing such commisures with a preset bending response.

A gradual response configuration of valve 20 includes a frame 24 or walls 26 or 28 that are configured capable of changing conformation in response to pressure elevation in a gradual or stepwise manner. In such cases, diameter of opening 22 of valve 20 can increase from 1-3 mm (closed state) in increments of, for example, 1 mm in response to changes in pressure of 5 mmHg.

In the configuration shown in FIGS. 1A-2B, valve 20 is capable of a gradual opening response to increases left chamber pressure. Such gradual response is enabled by use of arms 30 forming a part of frame 24. As is shown in FIGS. 2A-2B, pressure applied to front walls 26 of valve 20 rotates arms 30 inward (towards shunt 12) thereby increasing diameter of opening 22. In such a configuration, a rise in pressure of 5-10 mmHg (over a threshold, e.g. 25 mmHg in the LA), translates to an increase of 5-10 grams of force in walls 26 and rotation of arms 30 45 degrees inward. In a preferred configuration of device 10, rotation of arms 30 45 degrees inward results in an increase diameter in opening 22 from 3 to 5 mm.

FIG. 3 illustrates another embodiment of device 10. In this embodiment flow through shunt 12 is controlled by a sail-like element 40 which is disposed completely in the left Atrium. When the pressure in the LA rises above a predetermined threshold elements 42 are pushed towards the Septum. This movement pulls valve flaps 42 outward (in the direction of arrows 44) thereby increasing flow through shunt 12.

Although the above described embodiments of device 10 are presently preferred, additional embodiments of device 10 which can provide the functionality described herein are also envisaged. Any configuration which can be used to increase flow in shunt 12 as a function of Left chamber pressure increase can be used with the present invention. This includes a shunt 12 designed with a collapsible conduit (e.g. fabricated from soft, pliable silicone), which is forced open by pressure changes.

Device 10 of the present invention can be configured to support any flow capacity of therapeutic value and be capable of any response profile to increasing or decreasing chamber pressures. Preferably, device 10 supports a minimal flow capacity of 0.1-0.3 and a maximal flow capacity of 0.6-1.2 l/min under increased left chamber pressure. In cases of atrial implantation and conditions characterizing SHF, device 10 supports a flow capacity of 0.1-0.5 l/min at LAP of less than or equal to 25 mmHg and a flow capacity of 0.6-1.2 l/min at LAP greater than 25 mmHg. In cases of atrial implantation and conditions characterizing DHF, device 10 supports a flow capacity of 0.1-0.3 l/min at LAP of less than or equal to 25 mmHg and a flow capacity of 0.5-1.2 l/min at LAP greater than 25 mmHg. Such a pressure versus shunt diameter curve is not linear but is preferably exponential.

FIGS. 4A-4D illustrate yet another embodiments of device 10 of the present invention. The configuration exemplified by this embodiment is responsive (in as far as changes to flow capacity) to either LA-RA pressure differential or to left atrial pressure only as is the case with the configurations described above. In this configuration, valve 20 can fully close under low a pressure differential lower than a predetermined threshold or under LA pressure lower than a threshold. Such complete closure prevents any flow from the LA to the RA.

Figure 4A:
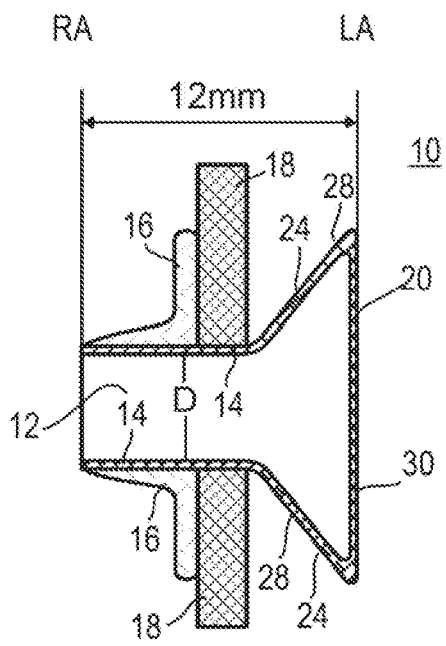
FIGS. 4A-D illustrate side (FIGS. 4A, 4C) and frontal (FIGS. 4B, 4D) views of another embodiment of the present device in closed (FIGS. 4A-4B) and open (FIGS. 4C-4D) positions.
Figure 4B:
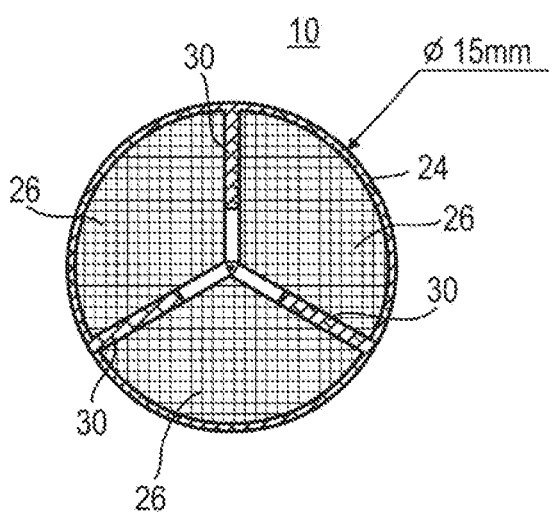
Figure 4C:
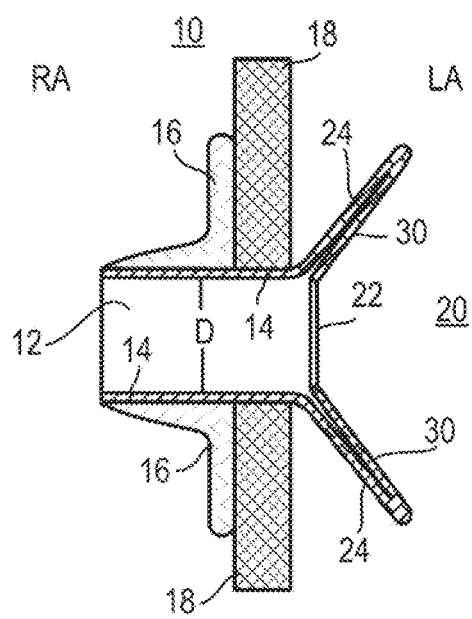
Figure 4D:
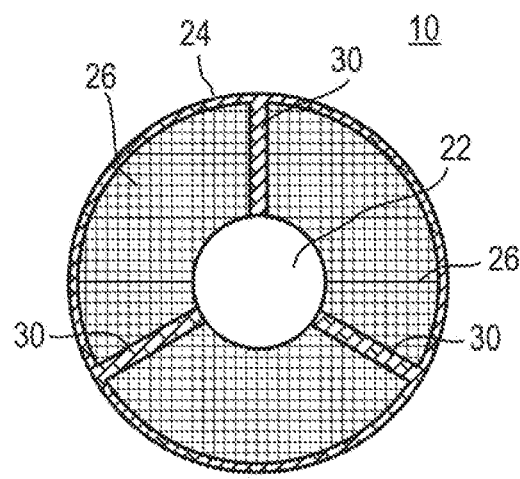

Components of device 10 are as described above. Valve 20 includes front walls 26 (leaflets) that are sutured to arms 30 (commisures). Arms 30 can be constructed from NITINOL which at a pressure differential higher than 8 mmHg (i.e. the pressure difference between the right and left sides of walls 26 as shown in FIG. 4a) will elastically deform in the direction of the RA to thereby open valve 20 and enable blood flow from the LA to the RA. Such opening of valve 20 can be gradual up to a maximum achieved at a pressure differential of 10 mmHg. Likewise when the pressure differential decreases to below 5 mmHg, valve 20 will close completely.

Valve 20 of this embodiment of device 10 opens and closes with each heart cycle as a response to an RA-LA pressure differential.

Such a pressure differential fluctuates between diastolic and systolic phases of each heart cycle. In chronic CHF patients, peak LA pressure is below 25 mmHg and thus the LA-RA pressure differential is around 5 mmHg in the diastolic phase and 10 mmHg in the systolic phase. Valve 20 is designed to start opening (Increasing flow capacity through shunt 12) at a pressure differential higher than 5 mmHg. As a result, in chronic CHF, shunt 12 will support maximal flow capacity at the systolic phase of each heart cycle and minimal flow capacity at the diastolic phase. This will result in a net flow (LA to RA) of less than 0.3 l/min.

During acute stages when the LA pressure is higher than 25 mmHg, valve 20 will be fully open, this will result in a net flow (LA to RA) of 1.5 l/min thereby decreasing the LA pressure by 5 mmHg.

FIGS. 5A-5D illustrate yet another configuration of device 10 of the present invention. In this configuration, shunt 12 is housed in a diabolo-shaped body which is constructed from an alloy such as stainless steel or NITINOL using methods well known in the art of stent making. A diabolo-shaped body is advantageous for septal anchoring and the prescribed function of device 10. A diabolo shape ensures that a device 10 positioned within a septum opening is trapped therein due to the fact that the region of minimal diameter of device 10 (indicated by 13 in FIGS. 5A-SD) traverses the septal opening while the larger diameter ends flank the opening and do not contact the tissue. This anchoring configuration also minimizes irritation to septal tissue since contact between device 10 and the tissue is minimized. Since the larger diameter ends (15 in FIGS. 5A-SD) of device 10 flank the septal opening and cannot move through the opening therein, device 10 is essentially trapped and secured within the opening. In addition, such trapping (passive anchoring) ensures that device 10 remains in position during septal wall movement, dilation of the septal opening and flow of blood through shunt 12 while accommodating such movement without applying forces to the septal tissue which might result in tissue damage.

The configuration of device 10 depicted in FIGS. 5A-5D also includes a valve 20 which is constructed from elastic arms 30 which can be separately connected to the body of device 10 (FIGS. 5C-5D) by way of welding, suturing, or interconnected at ends thereof into a single structure as shown in FIGS. SA-5B). Arms 30 can be covered with tissue or PTFE membranes (not shown) in a manner similar to that described above. Arms 30 can move between a closed position (as shown in FIGS. 5B-SC) which minimizes or blocks flow and one or more open positions (FIG. 5D) which support flow at predetermined flow rates according to a pressure or a pressure differential at valve 20 (The force of bending each arm until it reaches the stent is 5 grams). In this respect, valve 20 of this device 10 configuration functions in a manner similar to valve 20 described above with reference to alternative device 10 configurations.

Device 10 is delivered via a standard trans-septal puncture procedure. A trans-septal puncture is made as described below and a 12-16 F sheath is inserted into the septal opening from the RA venous system from the inferior vena Cava side. Device 10 is fed into the distal end of the sheath (protruding into the LA) via a tapered loader and pushed into the sheath to the point where the LA side of device 10 protrudes from the distal side of the sheath. The LA side of device 10 is then expanded (by pushing the valve into the LA). The sheath, with the device, is then pulled into the RA to the point where the expanded LA side of device 10 contacts the septum. In this position the sheath is pulled back (in the direction of the RA) exposing the RA side of device 10 and locking it within the septum. The Loader and sheath are then removed.

In the expanded configuration, device 10 is about 13 mm in length, with a minimal diameter of 4-8 mm (at 13) and a maximal diameter of 10-16 mm (at 15). In the compressed (deliverable) configuration, device 10 is 10-18 mm in length and 3-6 mm in diameter.

As is mentioned hereinabove, different patients may exhibit slightly different hemodynamic parameters (e.g. different left atrial pressure). Thus, to meet the needs of different patients, device 10 can be configured as part of a kit which includes several variants of device 10, each having slightly different characteristics (such as device 10 length, diameter of shunt 12, pressure threshold for increasing opening 22 of valve 20 and the like). Such a kit enables a physician to match a patient with the most suitable variant of device prior to implantation.

Alternatively, device 10 can be configured modifiable post implantation. Such a configuration of device 10 can include elements which can be adjusted post implantation to thereby modify device 10 characteristics to match the hemodynamic profile of the patient.

One example of such a configuration can include a device 10 which can have a shunt 12 conduit which can be expanded to a predetermined diameter suing a balloon catheter.

Preferred flow parameters of device 10 of the present invention are described in detail in Example 1 of the Examples section which follows.

As is mentioned hereinabove, device 10 of the present invention can be utilized in treatment of CHF as well as other disorders. In the case of CHF, device 10 is preferably positioned in a septum between atria using a minimally invasive delivery system.

Thus, according to another aspect of the present invention there is provided a system for regulating pressure in a heart chamber.

The system includes a delivery catheter capable of delivering device 10 to a heart septum and a sheath, a push-rod, a transeptal puncture device and haemostatic valves Implantation of device 10 is effected via transfemoral approach. A catheter is delivered through a sheath placed through the femoral vein and up into the Vena Cava into the RA. A transeptal puncture device is deployed from the delivery catheter and the middle of the Fossa Ovalis of the septum is controllably punctured and then dilated via a balloon catheter to 7 mm (switched through the sheath). A pressure transducer catheter is then used to collect hemodynamic parameters from the left and right atria over at least one complete heart cycle to thereby derive patient-specific parameters such as left atrial pressure during diastole and systole and the like. These parameters will enable selection of a device 10 having characteristics (e.g. flow capacity of shunt in the closed and folly open positions, length of device 10) which best match the needs of the patient.

The device 10 selected is then loaded onto a delivery catheter and delivered to the septum. Device 10 is pushed out of the access sheath and into the LA using the push-rod deployed from the delivery catheter, such positioning deploys the anchoring elements on the RA side. The catheter is then retracted to position the device in place in the LA and deploy the anchoring elements at the LA side.

Such transplantation of device 10 of the present invention through a septum of a subject can be used to treat CHF-related conditions as well as be used in cases of septal or atrial defects which cannot be effectively treated via standard approaches.

The present device can also be used to determine the pressure in the left atrium and thus assist in assessing the clinical condition of the patient. Such an assessment can be used to adjust the medication given to the patient and help stabilize the patient's hemodynamic condition.

Left atrial pressures can be determined by visualizing, using imaging modality such as echo ultrasound, an angle of the leaflets of the valve of the present device or by quantifying the flow across the valve. The angles of the leaflets or the flow across the valve will correlate to a specific pressure gradient between the left and right atrium thus correlate to the pressure in the left atrium. By quantifying the pressure in the left atrium the physician can adjust the medications given to the patient and help in stabilizing the hemodynamic condition of the patient and prevent edema. Example 4 of the Examples section which follows provides further detail with respect to leaflet angle and flow measurements calculations.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Flow Calculations

The present inventors have calculated the flow needed to reduce left atrial pressure (LAP) to below 25 mmHg. For the purpose of calculations it was assumed that under SHF and DHF, the LAP minimum and maximum pressures are the same (12 mmHg & 28 mmHg respectively). In order to treat these conditions, LAP must be reduced by 3-5 mmHg.

The following parameters were taken into consideration: (i) SHF cardiac output (CO)—2.5-4 l/min heart rate (HR)=75 (ii) DHF CO=3-5.5 l/min HR=70. In SHF one can assume a linear correlation between LA pressure and volume (Pstatic fluid=ρgh), and thus one can calculate the following:

In SHF: LAP—16 mmHg. Filling volume—50 cc each cycle. Reducing LAP by 3-5 mmHg i.e. 3⁵⁄₁₆=20%-30% requires 20%-30% less blood i.e. 10 cc-16 cc of blood each heart beat which translates to ~0.75 l/min to 1.2 l/min LA-RA flow in SHF [10 cc & 16 cc×75 (HR)]

To find an optimal shunt diameter, one can use Bernouli's equation and assume no viscosity due to the short length of the shunt (few mm at narrowest diameter):

$$Q = CeE \frac{\pi D_2^2}{4} \sqrt{\frac{2(P_1 - P_2)}{\rho}}$$

Where Q (Flow)=1.2 l/min, C (Discharge Coefficient)=0.7, e (expansion)=NA (for gasses only), P1-P2 (LAP-RAP after shunting)=6 mmHg, and ρ=1.05 gr/cm³.

A shunt diameter of 4 mm supports a flow capacity of 0.75 l/min, and a 3 mmHg reduction in LAP, a shunt diameter of 5.5 mm supports a flow capacity of 1.3 l/min & and a 5 mmHg reduction in LAP.

Once the shunt is positioned, the first few heart cycles will enable 1 l/min flow until the pressure is below 25 mmHg. When the shunt supports 1 l/min one can expect ~0.3 l/min CO reduction. This is because of the compensatory mechanisms in CHF.

Figure 7:
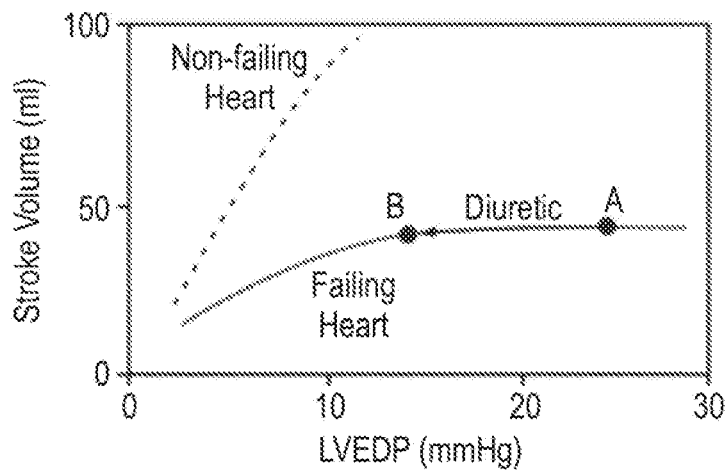
FIG. 7 is a curve illustrating a stroke volume—left ventricle end diastolic (LVED) pressure relationship in a failing and non-falling heart.
Figure 8:
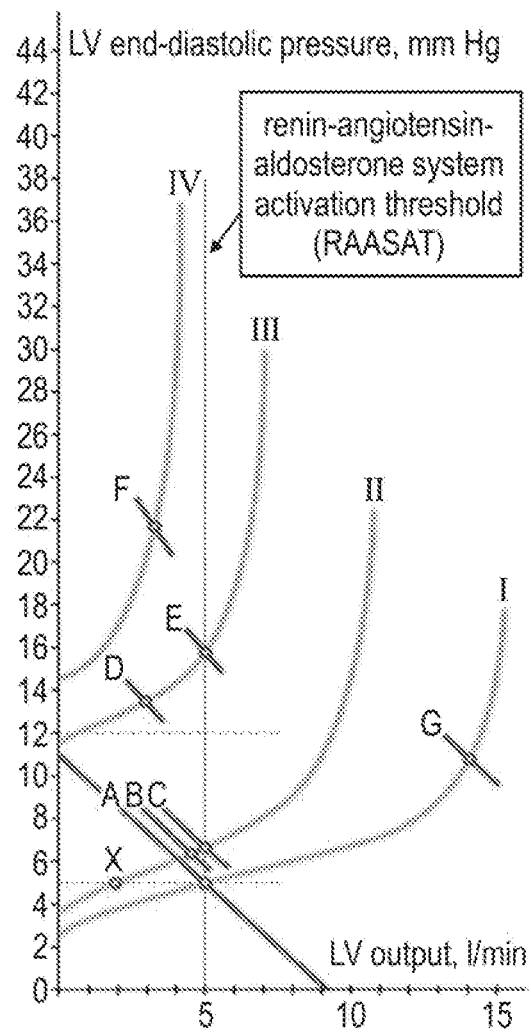
FIG. 8 is a curve illustrating a left ventricle end diastolic (LVED) pressure—left ventricle (LV) output relationship in patients classified according to the severity of the condition. Class I (Mild)—no limitation of physical activity. Ordinary physical activity does not cause undue fatigue, palpitation, or dyspnea (shortness of breath). Class II (Mild)—slight limitation of physical activity. Comfortable at rest, but ordinary physical activity results in fatigue, palpitation, or dyspnea. Class III (Moderate)—marked limitation of physical activity. Comfortable at rest, but less than ordinary activity causes fatigue, palpitation, or dyspnea. Class IV (Severe)—unable to carry out any physical activity without discomfort. Symptoms of cardiac insufficiency at rest. If any physical activity is undertaken, discomfort is increased.

Both in SHF and DHF the heart is working on the plateau of the Starling curve. The additional pressure is not correlated to additional stroke volume (FIG. 7). The additional volume is translated to high pressures and edema. Therefore by slightly reducing the filling volumes there will be a decrease in the pressure but not in the stroke volume.

These Figures (the right one for DHF and the left for SHF patients) show the correlation between end diastolic volumes (pressures) and stroke volume in heart failure patients. It teaches us that in heart failure patients the high pressures are not correlated with stroke volume (Cardiac output). Therefore if we will shunt a certain amount of blood away from the left ventricle we will not reduce the cardiac output both in DHF and SHF patients.

By designing a shunt which changes in flow capacity as a function of LAP, the shunt diameter can reduce to 3 mm when LAP is below 25 mmHg. Under such conditions, Q will be ~0.35 V/min and the overall CO reduction is 0.35× 0.6/2-0.1 l/min in DHF and slightly less than 0.1 l/min in SHF (including compensation mechanisms).

Utilizing the parameters above to design a shunt ensures that during onset of Pulmonary Edema (PE), the shunt will open to 4 mm-5.5 mm and decrease LAP by 3 mmHg-5 mmHg. LA to RA flow will be 0.75 l/min-1 l/min. Under non-PE conditions, the shunt will remain patent just in the Atria's V-Wave and although the opening will be maximal it will only be for a short duration of 150 ms. As a result, LA-RA flow will be 0.3 l/min. the CO reduction will be less than 0.1 l/min Example 2

Construction and Deployment of One Embodiment of the Present Device

A device similar to the one illustrated in FIGS. 1A-2B is manufactured as follows. A NITINOL tube having a diameter of 5 mm, a length of 18 mm and a wall thickness of 0.25 mm is laser cut to create a tubular wire frame. The tubular frame is electro-polished and cleaned and then heat treated to set its final shape on a mandrel. The internal and external surfaces of the frame are wrapped with ePTFE. Valve leaflets are die cut from 0.25 mm thick bovine pericardium tissue and sutured to form a partially open leaflet valve which is then sutured onto the tubular frame over the fabric at the funnel opening. The resultant device is packed until use under sterile conditions. Prior to transplantation, the device is unpacked and collapsed by hand or by a crimping tool to a final diameter of less than 13F, the collapsed device is loaded into a catheter and placed in front of a pusher rod fitted into the catheter. The device is then positioned as described hereinabove.

Example 3

Construction and Testing of a Diabolo-Shaped Device

Figure 6A:
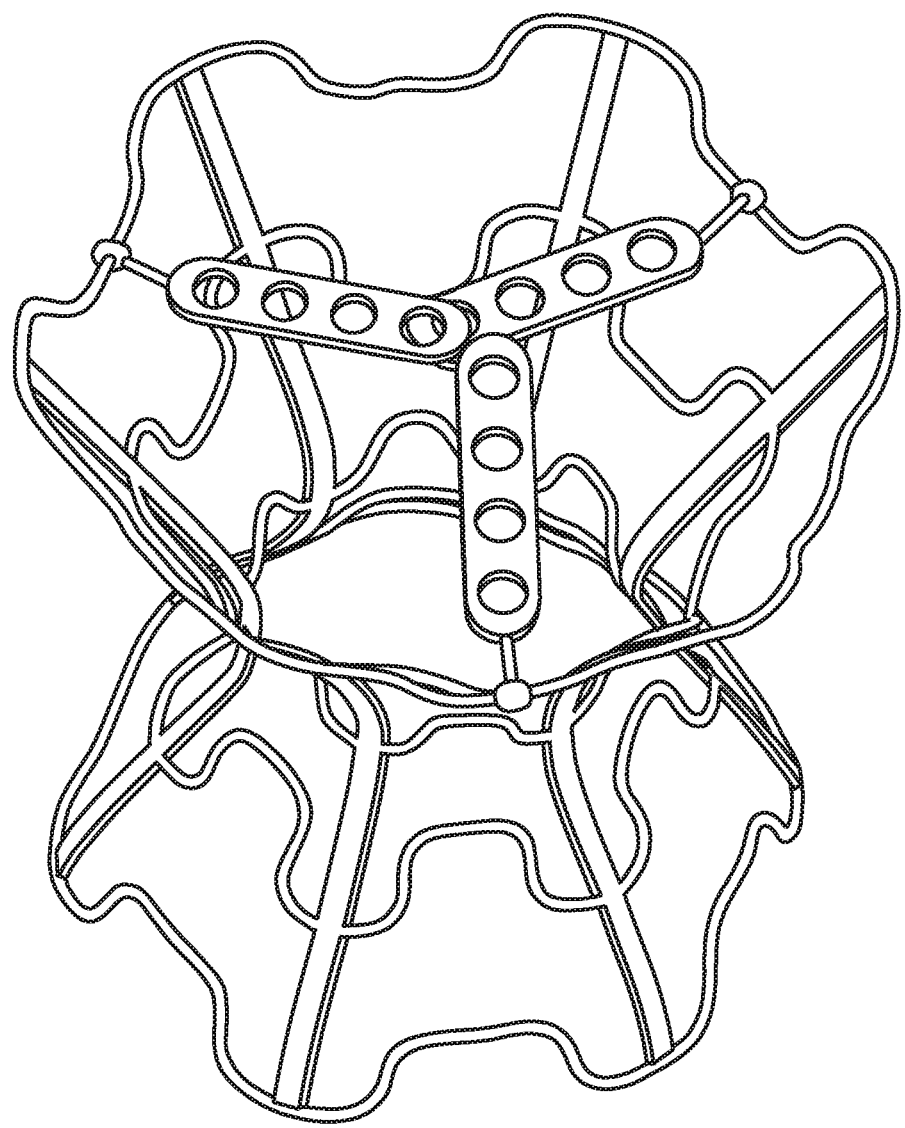
FIGS. 6A-6B illustrate the diabolo-shaped device of the present invention as a bare wire frame (FIG. 6A) and a PTFE/Pericard-covered wire frame (FIG. 6B).

A diabolo-shaped configuration of the present device was constructed by laser cutting a stent from Nitinol tubing and shaping the cut stent into a Diabolo by using a mandrel and applying 530° C. for 12 minutes. Bars for forming the valve arms were laser cut from a 0.0.09 mm thick Nitinol sheet and the bars were shaped using a mandrel. The shaped bars were then welded to the diabolo-shaped stent at three points encircling an opening of the stent. The bare wire frame form of the device is shown in FIG. 6A.

Figure 6B:

The stent was then covered with ePTFE impregnated with carbon and Pericard leaflets were sutured to the three bars and the circumference of the stent around the three bars (FIG. 6B). The finished device was then sterilized and collapsed for loading into a sheath.

The device shown in FIG. 6B was tested using the flow chamber described below to simulate the fluid pressures present in heart chambers. The device performed as specified i.e. when the valve was subjected to water pressure equivalent to a column of water >10 cm, the valve arms flexed inward and the valve opened to allow water flow at 0.5 l/min. Water pressure equivalent to a column of water <10 cm did not open the valve and thus did not result in any net water flow through the conduit (shunt) of the device.

Example 4

Leaflet Angle and Flow as a Function of Pressure Differentials

Figure 9A:
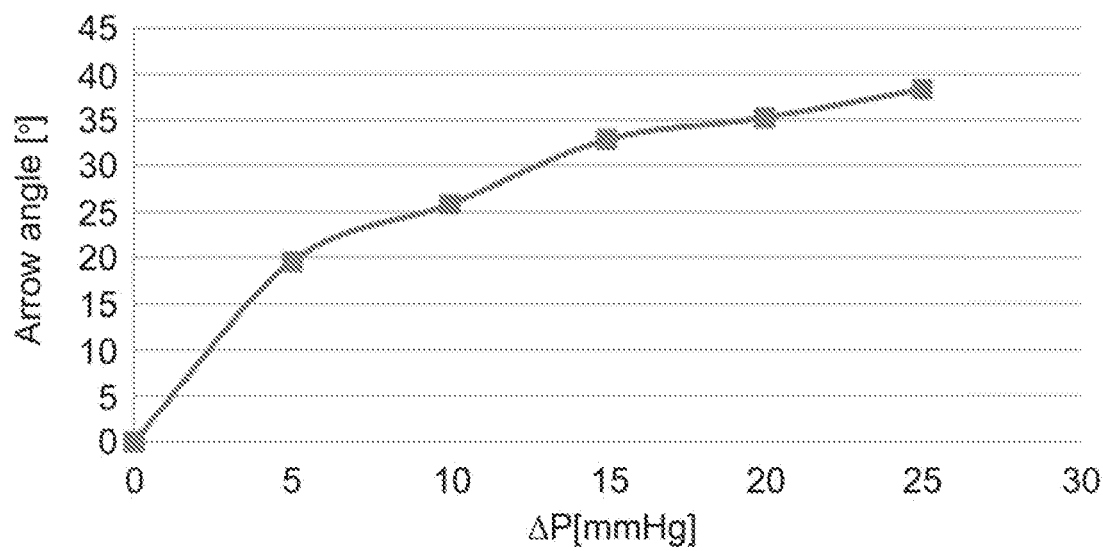
FIGS. 9A-9B illustrate the effect of a left atrium-right atrium pressure differential on leaflet opening angle (FIG. 9A) and flow rate (FIG. 9B).
Figure 9B:
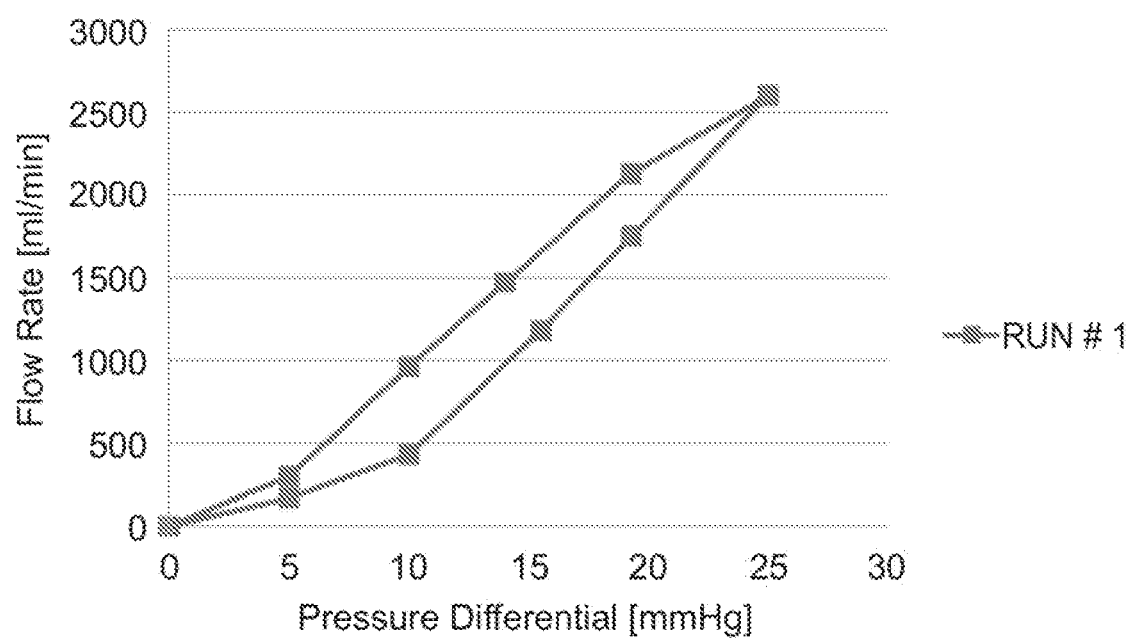

The present device was subjected to several pressure differentials using a flow chamber. Briefly, a two chambered device mimicking the left and right atria was constructed from plate Plexiglas. The device was positioned through a membrane separating the two chambers and water was pumped into the left chamber to generate a pressure gradient between the left and right chambers. Once the valve opened under the pressure of the water in the left chamber, water flowed into the right chamber and the flow rate was measured via a flow meter positioned on an output line connected to the bottom of the right chamber. The leaflet angle was determined by photographing the valve under the different pressure gradient conditions. Flow rates and leaflet angles were measured at several different pressure points from a first pressure at which the valve initially opens to a final pressure at which the valve was fully open. Leaflet angle and flow values obtained from six pressure differentials points were used to plot graphs (FIGS. 9A-9B).

Table 2 below exemplifies calculations of the leaflet angle at a 25 mmHg pressure differential.

TABLE 2

|  | X | Y |  | % of Diameter | % of original Length |  |
|---|---|---|---|---|---|---|
| Diameter | 6.24 | 1.09 | 6.334485 | 100 |  | angle |
| Arrow1 | 1.4 | 1.09 | 1.774289 | 28.00999 | 0.819125 | 35.00266 |
| Arrow2 | 1.14 | 0.37 | 1.198541 | 18.92089 | 0.738749 | 42.37504 |
| Arrow3 | 0.66 | 1.43 | 1.57496 | 24.86327 | 0.791299 | 37.69297 |
|  |  |  |  |  |  | 38.35689 |

As is shown by the FIGS. 9A-9B, a specific pressure differential (ΔP) can be correlated to a leaflet angle and a flow rate range.

Using the graph of FIG. 9A, a physician imaging the present device can convert an observed leaflet angle to a pressure differential. Alternatively, using the graph of FIG. 9B, a physician can translate an observed flow rate into a pressure differential. If desired, both graphs can be used to translate a leaflet angle to a flow rate and vise versa.

Therefore determining the leaflets angle or flow rate via, for example, imaging can provide a physician with an indication of pressure differential and as a result the pressure in the left atrium at any point in the heart cycle.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed:

1. A shunt for regulating blood pressure between a patient's left atrium and right atrium, the shunt comprising: a shunt conduit configured to be implanted at an atrial septum of the patient to dilate an opening in the atrial septum, the shunt conduit having an outer surface along a length greater than a thickness of the atrial septum, the shunt conduit configured to transition between a collapsed state suitable for percutaneous delivery and an expanded state when deployed across the patient's atrial septum such that the shunt conduit has a smallest diameter where the outer surface traverses the atrial septum and has a larger diameter at the outer surface where an end region of the shunt conduit extends into an atrium, wherein the shunt conduit has a diabolo shape and is configured to be collapsible after implantation.

2. The shunt of claim 1, further comprising an anchor configured to anchor the shunt conduit to the atrial septum when deployed.

3. The shunt of claim 1, wherein a flow rate capacity of the shunt conduit increases with an increase in pressure of the left atrium.

4. The shunt of claim 1, wherein the shunt conduit is configured to be expanded to a predetermined diameter using a balloon catheter.

5. The shunt of claim 1, wherein the diabolo shape of the shunt conduit is configured to prevent migration of the shunt conduit through the atrial septum when deployed.

6. The shunt of claim 1, wherein the shunt conduit is coated with expanded-polytetrafluoroethylene (ePTFE).

7. The shunt of claim 1, wherein the length of the shunt conduit is greater than twice the thickness of the atrial septum.

8. The shunt of claim 1, wherein the shunt conduit comprises a plurality of sinusoidal rings interconnected by a plurality of struts.

9. The shunt of claim 8, wherein the sinusoidal rings and struts further define a neck where the outer surface traverses the atrial septum between conical sections of the shunt conduit.

10. The shunt of claim 9, wherein the neck is between 4 and 6 mm in diameter.

11. The shunt of claim 1, wherein the shunt conduit is constructed from a nitinol frame.

12. The shunt of claim 1, wherein the shunt conduit defines a neck where the outer surface traverses the atrial septum between conical sections.

13. The shunt of claim 12, wherein the neck and the conical sections are collapsible.

14. The shunt of claim 12, wherein the neck is between 4 and 6 mm in diameter.

15. A method for regulating blood pressure between a patient's left atrium and right atrium, the method comprising:
implanting a shunt conduit at an atrial septum of the patient to dilate an opening in the atrial septum, the shunt conduit having an outer surface along a length greater than a thickness of the atrial septum, the shunt conduit configured to transition between a collapsed state suitable for percutaneous delivery and an expanded state when deployed across the patient's atrial septum such that the shunt conduit has a smallest diameter where the outer surface traverses the atrial septum and has a larger diameter at the outer surface where an end region of the shunt conduit extends into an atrium, wherein the shunt conduit has a diabolo shape and is configured to be collapsible after implantation.

16. The method of claim 15, further comprising expanding the shunt conduit to a predetermined diameter using a balloon catheter.

17. The method of claim 15, wherein the shunt conduit defines a neck where the outer surface traverses the atrial septum between conical sections.

18. The method of claim 17, wherein the neck and the conical sections are collapsible.

19. The method of claim 17, wherein the neck is between 4 and 6 mm in diameter.

20. The method of claim 15, further comprising shunting blood through the atrial septum via the shunt conduit to treat heart failure.

21. The shunt of claim 1, wherein the end region of the shunt conduit, when implanted in the expanded state, is configured to be disposed in the atrium and to not contact the atrial septum.

22. The shunt of claim 21, wherein the shunt conduit further comprises a second end region at an opposing end of the shunt conduit and having a larger diameter when deployed than the smallest diameter,
wherein the second end region of the shunt conduit, when implanted in the expanded state, is configured to be disposed in an opposing atrium and to not contact the atrial septum.

23. The method of claim 15, wherein the end region of the shunt conduit, when implanted in the expanded state, is disposed in the atrium and does not contact the atrial septum.

24. The method of claim 23, wherein the shunt conduit further comprises a second end region at an opposing end of the shunt conduit and having a larger diameter when deployed than the smallest diameter,
wherein the second end region of the shunt conduit, when implanted in the expanded state, is disposed in an opposing atrium and does not contact the atrial septum.

* * * * *